US010472630B2

(12) United States Patent
Lorson et al.

(10) Patent No.: US 10,472,630 B2
(45) Date of Patent: *Nov. 12, 2019

(54) SMN2 ELEMENT 1 ANTISENSE COMPOSITIONS AND METHODS AND USES THEREOF

(71) Applicant: The Curators of the University of Missouri, Columbia, MO (US)

(72) Inventors: Christian Lorson, Columbia, MO (US); Erkan Osman, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/858,421

(22) Filed: Dec. 29, 2017

(65) Prior Publication Data
US 2018/0148724 A1 May 31, 2018

Related U.S. Application Data

(63) Continuation of application No. 14/783,538, filed as application No. PCT/US2014/033856 on Apr. 11, 2014, now Pat. No. 9,885,040.

(60) Provisional application No. 61/853,820, filed on Apr. 12, 2013.

(51) Int. Cl.
*C12N 15/113* (2010.01)
(52) U.S. Cl.
CPC ........ *C12N 15/113* (2013.01); *C12N 2310/11* (2013.01); *C12N 2310/3233* (2013.01); *C12N 2320/33* (2013.01)
(58) Field of Classification Search
CPC .......................... C12N 15/113; A01K 2207/05
See application file for complete search history.

(56) References Cited

U.S. PATENT DOCUMENTS

| 5,882,868 A | 3/1999 | Funanage et al. |
| 6,867,349 B2 | 3/2005 | Ekker et al. |
| 7,468,418 B2 | 12/2008 | Iversen et al. |
| 9,885,040 B2 * | 2/2018 | Lorson ................. C12N 15/113 |
| 2004/0266720 A1 | 12/2004 | Iversen et al. |
| 2011/0118145 A1 | 5/2011 | Akmaev et al. |
| 2011/0294226 A1 | 12/2011 | Melki et al. |
| 2012/0190728 A1 | 7/2012 | Bennett et al. |
| 2015/0252364 A1 | 9/2015 | Krieg et al. |

FOREIGN PATENT DOCUMENTS

| EP | 2499262 A1 | 9/2012 |
| TW | 201007167 A | 2/2010 |
| WO | 01/66129 A1 | 9/2001 |
| WO | 2010120820 A1 | 10/2010 |
| WO | 2010148249 A1 | 12/2010 |
| WO | 2011060240 A1 | 5/2011 |
| WO | WO-2018014041 A2 * | 1/2018 ............ C07H 21/02 |

OTHER PUBLICATIONS

Baughan et al., "Delivery of Bifunctional RNAs that Target an Intronic Repressor and Increase SMN Levels in an Animal Model of Spinal Muscular Atrophy", Human Molecular Genetics, Feb. 19, 2009, pp. 1600-1611, vol. 18, No. 9.
Baughan, "Gene Therapy in Spinal Muscular Atrophy: RNA-Based Strategies to Modulate the Pre-mRNA Splicing of Survival Motor Neuron", Dissertation, Dec. 2008, pp. 1-154, retrieved from the internet, https://mospace.umsystem.edu/xmlui/bitstream/handle/10355/6686/research.df?sequence=3.
Butchbach et al., "A Novel Method for Oral Delivery of Drug Compounds to the Neonatal SMND7 Mouse Model of Spinal Muscular Atrophy", Journal of Neuroscience Methods, Apr. 15, 2007, pp. 285-290, vol. 161, No. 2.
Coady et al., "Development of a Single Vector System that Enhances Trans-Splicing of SMN2 Transcripts", PLoS One, Oct. 2008, 11 pages , vol. 3, Issue 10.
Cobb et al., "Development and Characterization of an SMN2-Based Intermediate Mouse Model of Spinal Muscular Atrophy", Human Molecular Genetics, 2013, pp. 1843-1855, vol. 22, No. 9.
Extended European Search Report for EP Application 14783392.5 dated Dec. 13, 2016.
Foust et al., "Rescue of the Spinal Muscular Atrophy Phenotype in a Mouse Model by Early Postnatal Delivery of SMN", Nature Biotechnology, Mar. 2010, pp. 271-274, vol. 28, No. 3.
Hua et al., "Antisense Masking of an hnRNP A1/A2 Intronic Splicing Silencer Corrects SMN2 Splicing in Transgenic Mice", The American Journal of Human Genetics, Apr. 2008, pp. 834-848, vol. 82.
Hua et al., "Peripheral SMN Restoration is Essential for Long-Term Rescue of a Severe SMA Mouse Model", Nature., Apr. 6, 2012, pp. 123-126, vol. 478, No. 7367.
Hua et al., "Peripheral SMN Restoration is Essential for Long-Term Rescue of a Severe Spinal Muscular Atrophy Mouse Model", Nature, Oct. 6, 2011, pp. 123-126, vol. 478.
International Search Report and Written Opinion for PCT/US2014/033856 dated Sep. 24, 2014.
Le et al., "SMND7, the Major Product of the Centromeric Survival Motor Neuron (SMN2) Gene, Extends Survival in Mice with Spinal Muscular Atrophy and Associates with Full-Length SMN", Human Molecular Genetics, 2005, pp. 845-857, vol. 14, No. 6.

(Continued)

*Primary Examiner* — Brian Whiteman
(74) *Attorney, Agent, or Firm* — Thompson Coburn LLP; William A. Holtz

(57) ABSTRACT

The invention provides methods and compositions for treatment of spinal muscular atrophy (SMA). In one aspect of the invention, a series of compositions comprising an antisense oligonucleotide targeting the Element 1 site on the SMN2 pre-mRNA and a Morpholino backbone is disclosed. In another aspect of the invention, a method of treating SMA patients by modulating the splicing of SMN2 pre-mRNA to increase the amount of full-length SMN is disclosed. Certain embodiments of the inventive method comprise administering an E1-targeting antisense oligonucleotide, such as Morpholino based antisense oligonucleotide, to a SMA subject.

10 Claims, 36 Drawing Sheets
Specification includes a Sequence Listing.

(56) References Cited

OTHER PUBLICATIONS

Lewelt et al., "New Therapeutic Approaches to Spinal Muscular Atrophy", Current Neurology and Neuroscience Reports, 2012, pp. 42-53, vol. 12, No. 1.

Ling et al., "Severe Neuromuscular Denervation of Clincally Relevant Muscles in a Mouse Model of Spinal Muscular Atrophy", Human Molecular Genetics, 2012, pp. 185-195, vol. 21, No. 1.

Lorson et al., "A Single Nucleotide in the SMN Gene Regulates Splicing and is Responsible for Spinal Muscular Atrophy", Proceedings of the National Academy of Sciences, May 1999, pp. 6307-6311, vol. 96.

Lorson et al., "SMN-Inducing Compounds for the Treatment of Spinal Muscular Atrophy", Future Medicinal Chemistry, Oct. 2012, pp. 2067-2084, vol. 4, No. 16.

Meister et al., "SMN-Mediated Assembly of RNPs: A Complex Story", Trends in Cell Biology, Oct. 10, 2002, pp. 472-478, vol. 12, No. 10.

Miyajima et al., "Identification of a Cis-Acting Element for the Regulation of SMN Exon 7 Splicing", The Journal of Biological Chemistry, Jun. 28, 2002, pp. 23271-23277, vol. 277, No. 26.

Miyaso et al., "An Intronic Splicing Enhance Element in Survival Motor Neuron (SMN Pre-mRNA", The Journal of Biological Chemistry, May 2, 2003, pp. 15825-15831, vol. 278 No. 18.

Monani et al., "A Single Nucleotide Difference that Alters Splicing Patterns Distinguishes the SMA Gene SMN1 from the Copy Gene SMN2", Human Molecular Genetics, 1999, pp. 1177-1183, vol. 8, No. 7.

Naryshkin et al., "SMN2 Splicing Modifiers Improve Motor Function and Longevity in Mice with Spinal Muscular Atrophy", Science, Aug. 8, 2014, pp. 688-693, vol. 345, Issue 6197.

Nlend et al., "Repair of Pre-mRNA Splicing Prospects for a Therapy for Spinal Muscular Atrophy", RNA Biology, Aug. 2010, pp. 430-440, vol. 7 No. 4.

Osborne et al., "Reference Guide to Mouse Models of Spinal Muscular Atrophy", The Jackson Laboratory, Jun. 2013, 22 pages.

Osman, et al., "Bifunctional RNAs Targeting the Intronic Splicing Silencer N1 Increase SMN Levels and Reduce Disease Severity in an Animal Model of Spinal Muscular Atrophy", The American Society of Gene & Cell Therapy, Jan. 2012, pp. 119-126, vol. 20, No. 1.

Palacino et al., "SMN2 Splice Modulators Enhance U1-pre-mRNA Association and Resuce SMA Mice", Nature Chemical Biology, Jul. 2015, pp. 511-517, vol. 11.

Passini et al., "Antisense Oligonucleotides Delivered to the Mouse CNS Ameliorate Symptoms of Severe Spinal Muscular Atrophy", Science Translational Medicine, Mar. 2, 2011, pp. 1-21, vol. 3, No. 72.

Pellizzoni et al., "Essential Role for the SMN Complex in the Specificity of snRNP Assembly", Science, Nov. 29, 2002, pp. 1775-1779, vol. 298, No. 5599.

Porensky et al., "A Single Administration of Morpholino Antisense Oligomer Rescues Spinal Muscular Atrophy in Mouse", Human Molecular Genetics, 2012, pp. 1625-1638, vol. 21, No. 7.

Rigo et al., "Antisense-Based Therapy for the Treatment of Spinal Muscular Atrophy", The Journal of Cell Biology, Oct. 1, 2012, pp. 21-25, vol. 199, No. 1.

Schindelin et al., Fiji—An Open Source Platform for Biological Image Analysis, Nature Methods, Dec. 7, 2013, pp. 1-15, vol. 9, No. 7.

Schindelin et al., "Fiji: An Open-Source Platform for Biological-Image Analysis", Nature Methods, Jul. 2012, pp. 676-682, vol. 9, No. 7.

Summerton et al., "Morpholino and Phosphorothioate Antisense Oligomers Compared in Cell-Free and In-Cell Systems", Antisense and Nucleic Acid Drug Development, 1997, pp. 63-70, vol. 7.

Summerton et al., "Morpholino, siRNA, and S-DNA Compared: Impact of Structure and Mechanism fo Action on Off-Target Effects and Sequence Specificity", Current Topics in Medicinal Chemistry, 2007, pp. 651-660, vol. 7.

\* cited by examiner

FIG. 2

Western Blot Analysis

RT-PCR for SMN-Full Length and SMN-Δ7

SEQUENCE LISTING

```
<160> NUMBER OF SEQ ID NOS: 45

<210> SEQ ID NO 1
<211> LENGTH: 222
<212> TYPE: DNA
<213> ORGANISM: Homo sapiens

<400> SEQUENCE: 1
tgcaagaaaa ccttaactgc agcctaataa ttgttttctt tgggataact tttaaagtac    60
attaaaagac tatcaactta atttctgatc atattttgtt gaataaaata agtaaaatgt   120
cttgtgaaac aaaatgcttt ttaacatcca tataaagcta tctatatata gctatctatg   180
tctatatagc tattttttt aacttccttt attttcctta ca                       222

<210> SEQ ID NO 2
<211> LENGTH: 45
<212> TYPE: DNA
<213> ORGANISM: Homo sapiens

<400> SEQUENCE: 2
gtaaaatgtc ttgtgaaaca aaatgctttt taacatccat ataaa                    45

<210> SEQ ID NO 3
<211> LENGTH: 87
<212> TYPE: DNA
<213> ORGANISM: Homo sapiens

<400> SEQUENCE: 3
atattttgtt gaataaaata agtaaaatgt cttgtgaaac aaaatgcttt ttaacatcca    60
tataaagcta tctatatata gctatct                                        87

<210> SEQ ID NO 4
<211> LENGTH: 87
<212> TYPE: DNA
<213> ORGANISM: Homo sapiens

<400> SEQUENCE: 4
tctatcgata tatctatc gaaatatacc tacaattttt cgtaaaacaa agtgttctgt     60
aaaatgaata aaataagttg ttttata                                        87

<210> SEQ ID NO 5
<211> LENGTH: 39
```

```
<212> TYPE: DNA
<213> ORGANISM: Homo sapiens

<400> SEQUENCE: 5
ctatatatag atagttattc aacaaaacta gtaattttt                    39

<210> SEQ ID NO 6
<211> LENGTH: 26
<212> TYPE: DNA
<213> ORGANISM: Homo sapiens

<400> SEQUENCE: 6
ctatatatag atagttattc aacaaa                                  26

<210> SEQ ID NO 7
<211> LENGTH: 25
<212> TYPE: DNA
<213> ORGANISM: Homo sapiens

<400> SEQUENCE: 7
tagatagctt tacattttac ttatt                                   25

<210> SEQ ID NO 8
<211> LENGTH: 25
<212> TYPE: DNA
<213> ORGANISM: Homo sapiens

<400> SEQUENCE: 8
tatggatgtt aaaaagcatt ttgtt                                   25

<210> SEQ ID NO 9
<211> LENGTH: 25
<212> TYPE: DNA
<213> ORGANISM: Homo sapiens

<400> SEQUENCE: 9
ctatatatag atagctttat atgga                                   25

<210> SEQ ID NO 10
<211> LENGTH: 25
<212> TYPE: DNA
<213> ORGANISM: Homo sapiens

<400> SEQUENCE: 10
cattttactt attttattca acaaa                                   25

<210> SEQ ID NO 11
<211> LENGTH: 25
<212> TYPE: DNA
<213> ORGANISM: Homo sapiens

<400> SEQUENCE: 11
gctttatatg gacattttac ttatt                                   25

<210> SEQ ID NO 12
<211> LENGTH: 25
<212> TYPE: DNA
<213> ORGANISM: Homo sapiens

<400> SEQUENCE: 12
gatgttaaaa agcgtttcac aagac                                   25

<210> SEQ ID NO 13
```

-continued

```
<211> LENGTH: 25
<212> TYPE: DNA
<213> ORGANISM: Homo sapiens

<400> SEQUENCE: 13
tatatggatg ttattattca acaaa                                      25

<210> SEQ ID NO 14
<211> LENGTH: 25
<212> TYPE: DNA
<213> ORGANISM: Homo sapiens

<400> SEQUENCE: 14
gcattttgtt tcacaagtta ttcaa                                      25

<210> SEQ ID NO 15
<211> LENGTH: 25
<212> TYPE: DNA
<213> ORGANISM: Homo sapiens

<400> SEQUENCE: 15
ctatatatag atagcgacat tttac                                      25

<210> SEQ ID NO 16
<211> LENGTH: 26
<212> TYPE: DNA
<213> ORGANISM: Homo sapiens

<400> SEQUENCE: 16
agatagcttt atatggattt attcaa                                     26

<210> SEQ ID NO 17
<211> LENGTH: 20
<212> TYPE: DNA
<213> ORGANISM: Homo sapiens

<400> SEQUENCE: 17
ctatatatag ttattcaaca                                            20

<210> SEQ ID NO 18
<211> LENGTH: 24
<212> TYPE: DNA
<213> ORGANISM: Homo sapiens

<400> SEQUENCE: 18
tttatatgga tgaagacatt ttac                                       24

<210> SEQ ID NO 19
<211> LENGTH: 24
<212> TYPE: DNA
<213> ORGANISM: Mus musculus

<400> SEQUENCE: 19
tctgtgttcg tgcgtggtga cttt                                       24

<210> SEQ ID NO 20
<211> LENGTH: 24
<212> TYPE: DNA
<213> ORGANISM: Mus musculus

<400> SEQUENCE: 20
cccaccacct aagaaagcct caat                                       24
```

```
<210> SEQ ID NO 21
<211> LENGTH: 24
<212> TYPE: DNA
<213> ORGANISM: Mus musculus

<400> SEQUENCE: 21
ccaacttaat cgccttgcag caca                                              24

<210> SEQ ID NO 22
<211> LENGTH: 24
<212> TYPE: DNA
<213> ORGANISM: Mus musculus

<400> SEQUENCE: 22
aagcgagtgg caacatggaa atcg                                              24

<210> SEQ ID NO 23
<211> LENGTH: 25
<212> TYPE: RNA
<213> ORGANISM: Artificial Sequence
<220> FEATURE:
<223> OTHER INFORMATION: Synthetic

<400> SEQUENCE: 23
ccucuuaccu caguuacaau uuaua                                             25

<210> SEQ ID NO 24
<211> LENGTH: 26
<212> TYPE: RNA
<213> ORGANISM: Homo sapiens

<400> SEQUENCE: 24
cuauauauag auaguuauuc aacaaa                                            26

<210> SEQ ID NO 25
<211> LENGTH: 14
<212> TYPE: RNA
<213> ORGANISM: Homo sapiens

<400> SEQUENCE: 25
cuauauauag auag                                                         14

<210> SEQ ID NO 26
<211> LENGTH: 12
<212> TYPE: RNA
<213> ORGANISM: Homo sapiens

<400> SEQUENCE: 26
uuauucaaca aa                                                           12

<210> SEQ ID NO 27
<211> LENGTH: 15
<212> TYPE: RNA
<213> ORGANISM: Homo sapiens

<400> SEQUENCE: 27
cuuucauaau gcugg                                                        15

<210> SEQ ID NO 28
<211> LENGTH: 18
<212> TYPE: RNA
<213> ORGANISM: Homo sapiens

<400> SEQUENCE: 28
```
ucacuuucau aaugcugg                                                          18

<210> SEQ ID NO 29
<211> LENGTH: 20
<212> TYPE: RNA
<213> ORGANISM: Homo sapiens

<400> SEQUENCE: 29
auucacuuuc auaaugcugg                                                        20

<210> SEQ ID NO 30
<211> LENGTH: 20
<212> TYPE: RNA
<213> ORGANISM: Homo sapiens

<400> SEQUENCE: 30
auucacuuuc auaaugcugg                                                        20

<210> SEQ ID NO 31
<211> LENGTH: 21
<212> TYPE: RNA
<213> ORGANISM: Homo sapiens

<400> SEQUENCE: 31
gauucacuuu cauaaugcug g                                                      21

<210> SEQ ID NO 32
<211> LENGTH: 25
<212> TYPE: RNA
<213> ORGANISM: Homo sapiens

<400> SEQUENCE: 32
guuagauuca cuuucauaau gcugg                                                  25

<210> SEQ ID NO 33
<211> LENGTH: 87
<212> TYPE: DNA
<213> ORGANISM: Homo sapiens

<400> SEQUENCE: 33
atattttgtt gaataaaata agtaaaatgt cttgtgaaac aaaatgcttt ttaacatcca            60
tataaagcta tctatatata gctatct                                                87

<210> SEQ ID NO 34
<211> LENGTH: 87
<212> TYPE: DNA
<213> ORGANISM: Homo sapiens

<400> SEQUENCE: 34
atattttgtt gaataaaata agtaaaatgt cttgtgaaac aaaatgcttt ttaacatcca            60
tataaagcta tctatatata gctatct                                                87

<210> SEQ ID NO 35
<211> LENGTH: 87
<212> TYPE: DNA
<213> ORGANISM: Homo sapiens

<400> SEQUENCE: 35
atattttgtt gaataaaata agtaaaatgt cttgtgaaac aaaatgcttt ttaacatcca            60
tataaagcta tctatatata gctatct                                                87

<210> SEQ ID NO 36
<211> LENGTH: 87
<212> TYPE: DNA
<213> ORGANISM: Homo sapiens

<400> SEQUENCE: 36

```
atattttgtt gaataaaata agtaaaatgt cttgtgaaac aaaatgcttt ttaacatcca    60
tataaagcta tctatatata gctatct                                        87
```

<210> SEQ ID NO 37
<211> LENGTH: 87
<212> TYPE: DNA
<213> ORGANISM: Homo sapiens

<400> SEQUENCE: 37

```
atattttgtt gaataaaata agtaaaatgt cttgtgaaac aaaatgcttt ttaacatcca    60
tataaagcta tctatatata gctatct                                        87
```

<210> SEQ ID NO 38
<211> LENGTH: 87
<212> TYPE: DNA
<213> ORGANISM: Homo sapiens

<400> SEQUENCE: 38

```
atattttgtt gaataaaata agtaaaatgt cttgtgaaac aaaatgcttt ttaacatcca    60
tataaagcta tctatatata gctatct                                        87
```

<210> SEQ ID NO 39
<211> LENGTH: 87
<212> TYPE: DNA
<213> ORGANISM: Homo sapiens

<400> SEQUENCE: 39

```
atattttgtt gaataaaata agtaaaatgt cttgtgaaac aaaatgcttt ttaacatcca    60
tataaagcta tctatatata gctatct                                        87
```

<210> SEQ ID NO 40
<211> LENGTH: 87
<212> TYPE: DNA
<213> ORGANISM: Homo sapiens

<400> SEQUENCE: 40

```
atattttgtt gaataaaata agtaaaatgt cttgtgaaac aaaatgcttt ttaacatcca    60
tataaagcta tctatatata gctatct                                        87
```

<210> SEQ ID NO 41
<211> LENGTH: 87
<212> TYPE: DNA
<213> ORGANISM: Homo sapiens

<400> SEQUENCE: 41

```
atattttgtt gaataaaata agtaaaatgt cttgtgaaac aaaatgcttt ttaacatcca    60
tataaagcta tctatatata gctatct                                        87
```

<210> SEQ ID NO 42
<211> LENGTH: 87
<212> TYPE: DNA
<213> ORGANISM: Homo sapiens

<400> SEQUENCE: 42

```
atattttgtt gaataaaata agtaaaatgt cttgtgaaac aaaatgcttt ttaacatcca      60
tataaagcta tctatatata gctatct                                         87

<210> SEQ ID NO 43
<211> LENGTH: 87
<212> TYPE: DNA
<213> ORGANISM: Homo sapiens

<400> SEQUENCE: 43
atattttgtt gaataaaata agtaaaatgt cttgtgaaac aaaatgcttt ttaacatcca      60
tataaagcta tctatatata gctatct                                         87

<210> SEQ ID NO 44
<211> LENGTH: 87
<212> TYPE: DNA
<213> ORGANISM: Homo sapiens

<400> SEQUENCE: 44
atattttgtt gaataaaata agtaaaatgt cttgtgaaac aaaatgcttt ttaacatcca      60
tataaagcta tctatatata gctatct                                         87

<210> SEQ ID NO 45
<211> LENGTH: 87
<212> TYPE: DNA
<213> ORGANISM: Homo sapiens

<400> SEQUENCE: 45
atattttgtt gaataaaata agtaaaatgt cttgtgaaac aaaatgcttt ttaacatcca      60
tataaagcta tctatatata gctatct                                         87
```

SMN2 ELEMENT 1 ANTISENSE COMPOSITIONS AND METHODS AND USES THEREOF

CROSS-REFERENCE TO RELATED APPLICATIONS

This application is a Continuation of U.S. National Phase application Ser. No. 14/783,538, filed Oct. 9, 2015, which claims priority to PCT/US2014/033856, filed Apr. 11, 2014, which claims the benefit of U.S. Provisional Application No. 61/853,820, filed Apr. 12, 2013, all of which are incorporated herein by reference in their entireties.

STATEMENT REGARDING FEDERALLY SPONSORED RESEARCH

This invention was made with Government support under Grant number RO1NS041584 awarded by the National Institutes of Health. The Government has certain rights in the invention.

INCORPORATION OF SEQUENCE LISTING

A Sequence Listing is contained in the file named UMC_149876_US_Substitute Sequence Listing_ST25.txt" which is 8,420 bytes (measured in MS-Windows) and comprising 45 nucleic acid sequences, created Mar. 13, 2017, is electronically filed herewith and is incorporated herein by reference in its entirety.

FIELD OF INVENTION

The present invention relates to methods and compositions for treating Spinal Muscular Atrophy (SMA), more specifically to a genetic therapy based on Element 1 antisense of SMN2 and Morpholino chemistry.

BACKGROUND OF INVENTION

Spinal Muscular Atrophies are collectively the second most common autosomal recessive neurodegenerative group of disorders with an incidence of 1 in 6000 (Crawford, T. O. and Pardo, C. A., 1996) and a carrier frequency of ~1 in 35 (Feldkotter, M. et al., 2002). The diseases are caused by the loss of α-motor neurons resulting in subsequent atrophy of voluntary muscle groups leading to paralysis and eventually to premature infantile death. Genetically the types of SMA result from a homozygous loss or mutation in the telomeric copy of the Survival Motor Neuron-1 (SMN1) gene. All SMA patients rely on the nearly identical copy gene, SMN2, which produces low levels of functional SMN protein. SMN is ubiquitously expressed and is a critical factor in a variety of RNA pathways. The best characterized SMN activity is in the assembly and maturation of the spliceosomal UsnRNPs (Meister, G., et al., 2002; Pellizzoni, L., et al., 2002). Even though the SMN2 gene is 99% identical in nucleotide sequence and is completely identical in amino acid sequence, approximately 90% of SMN2-derived transcripts are alternatively spliced and encode a truncated protein lacking the final coding exon (exon 7). This aberrant splicing event is the result of a silent, non-polymorphic C to T nucleotide transition 6 nucleotides within exon 7 (Lorson, C. L., et al., 1999; Monani, U. R., et al., 1999). SMN2, however, is an excellent target for therapeutic intervention.

Cis-acting negative regulatory regions that surround SMN2 exon 7 have been identified and described (Lorson, C. L., et al., 1999; Miyaso, H., et al., 2003; Miyajima, H., et al., 2002). In particular, ISS-N1 has been a hotspot for experimental therapeutics, especially antisense oligonucleotides (ASOs). ASO molecules of various lengths and backbone chemistries have been used to inhibit the repressor activity of ISS-N1, leading to an increase in SMN protein and significant extensions in survival in animal models of SMA. For example, one such approach is described in U.S. Pat. No. 8,110,560 B2 to Singh et al., which discloses a series of oligonucleotide reagents that effectively target the SMN2 ISS-NI site in the SMN2 pre-mRNA. U.S. Pat. No. 8,110,560 teaches that the ISS-N 1 blocking agents target the SMN2 pre-mRNA to modulate the splicing of SMN2 to include exon 7. 2'-MOE chemistry has been used by ISIS Pharmaceuticals in the development of their ASO, SMN-Rx (Hua, Y., et al., 2011; Rigo, F., et al., 2012). Similar Morpholino-based ASOs have shown excellent pre-clinical promise in severe SMA mice and are under further development.

Still, no effective treatment exists for SMA, and the complexity and expansive clinical spectrum suggests that the SMA community cannot solely rely upon a single lead compound or genetic target.

SUMMARY OF INVENTION

One aspect of the invention is drawn to a composition for blocking the repressive activity of the Element 1 of the SMN2 pre-mRNA. Such a composition comprises an antisense oligonucleotide that comprises a sequence annealing to a first region and a second region of the SMN2 pre-mRNA. The first region is flanked by certain nucleotides, that is, the first region of the SMN2 pre-mRNA is defined by or consists of the nucleotides between −134 to −90 relative to exon 7 of the SMN2 pre-mRNA. The second region is flanked by certain nucleotides, that is, the second region of the SMN2 pre-mRNA is defined by or consists of the nucleotides between −105 to −45 relative to exon 7 of the SMN2 pre-mRNA. In certain embodiments, the antisense oligonucleotide comprises or consists of a nucleic acid sequence selected from the group consisting of SEQ ID NO: 17 (v1.11), SEQ ID NO: 16 (v1.10), SEQ ID NO: 6 (v1.00), SEQ ID NO: 7 (v1.01), SEQ ID NO: 8 (v1.02), SEQ ID NO: 9 (v1.03), SEQ ID NO: 10 (v1.04), SEQ ID NO: 11 (v1.05), SEQ ID NO: 12(v1.06), SEQ ID NO: 13(v1.07), SEQ ID NO: 14 (v1.08). SEQ ID NO: 15 (v1.09), and SEQ ID NO: 18 (v1.12).

In certain embodiments, the antisense oligonucleotide comprises a nucleotide sequence that is complementary to at least eight consecutive nucleotides of the first region of the SMN2 pre-mRNA and is complementary to at least eight consecutive nucleotides of the second region of the SMN2 pre-mRNA. In certain embodiments, the sequence of the antisense oligonucleotide that is complementary to the second region of the SMN2 pre-mRNA is 5' of the sequence of the antisense nucleotide that is complementary to the first region of the SMN2 pre-mRNA.

In certain embodiments, the antisense oligonucleotide is not entirely complementary to the SMN2 pre-mRNA and contains one or more substitutions. For example in certain embodiments, the antisense oligonucleotide comprises:

i. a nucleotide sequence that is complementary to, except for having one or two nucleotide substitutions, at least eight consecutive nucleotides of the first region of the SMN2 pre-mRNA and is complementary to at least eight consecutive nucleotides of the second region of the SMN2 pre-mRNA;

ii. a nucleotide sequence that is complementary to at least eight consecutive nucleotides of the first region of the SMN2 pre-mRNA and that is complementary, except for having one or two nucleotide substitutions, to at least eight consecutive nucleotides of the second region of the SMN2 pre-mRNA; or iii. a nucleotide sequence that is complementary to, except for having one or two nucleotide substitutions, at least eight consecutive nucleotides of the first region of the SMN2 pre-mRNA and that is complementary, except for having one or two nucleotide substitutions, to at least eight consecutive nucleotides of the second region of the SMN2 pre-mRNA.

In certain embodiments, the antisense oligonucleotide comprises a nucleic acid sequence selected from the group consisting of SEQ ID NO: 17 (v1.11), SEQ ID NO: 16 (v1.10), SEQ ID NO: 6 (v1.00), SEQ ID NO: 7 (v1.01), SEQ ID NO: 11 (v1.05), SEQ ID NO: 12(v1.06), SEQ ID NO: 13(v1.07), SEQ ID NO: 14 (v1.08). SEQ ID NO: 15 (v1.09), and SEQ ID NO: 18 (v1.12).

Certain aspects of the invention are drawn to methods for blocking the repressive activity of the Element 1 of the SMN2 pre-mRNA. In certain embodiments, such a method comprises administrating to a subject a composition for blocking the repressive activity of the Element 1 of the SMN2 pre-mRNA of the invention.

Certain aspects of the invention are drawn to methods for treating Spinal Muscular Atrophy (SMA) in a human SMA patient. In certain embodiments, such a method comprises the step of administrating to the patient an effective amount of a composition for blocking the repressive activity of the Element 1 of the SMN2 pre-mRNA of the invention.

Certain aspects of the invention are drawn to a composition for blocking the repressive activity of the Element 1 of the SMN2 pre-mRNA, wherein the compositions comprising an antisense oligonucleotide with a sequence annealing to a first region and a second region of the SMN2 pre-mRNA and wherein the first region consists of the nucleotides between −134 to −120 relative to exon 7 of the SMN2 pre-mRNA and the second region consists of the nucleotides between −67 to −54 relative to exon 7 of the SMN2 pre-mRNA.

Certain aspects of the invention are drawn to methods for blocking the repressive activity of the Element 1 of the SMN2 pre-mRNA, thereby modulating the splicing pattern of the SMN2 to generate full-length (exon-7-retaining) SMN comprising the step of administrating to a subject a composition comprising an antisense nucleotide with a sequence annealing to two distinct regions flanking E1 on the SMN2 pre-mRNA, whereas the regions consist of the nucleotides between −134 to −120 and −67 to −54 (relative to exon 7).

In one aspect of the invention, a series of compositions capable of blocking or inhibiting the repressive activity of the SMN2 splice silencing domain, Element 1 (E1), is described. In certain embodiments, the inventive E1 antisense oligonucleotide (ASO) anneals to two distinct regions of two distinct regions of the SMN2 pre-mRNA (intron 6 sequence), and in certain embodiments, relative to exon 7 of the SMN2 pre-mRNA, the inventive ASO anneals to: −134 to −120 and −67 to −54. In certain embodiments, the backbone for the inventive E1 ASO comprises Morphonlino residues.

In another aspect of the invention, a method of treating spinal muscular atrophy (SMA) in a subject is described. In certain embodiments, the inventive method for treating SMA comprises the step of administering to a subject an E1 ASO described herein in a dose effective to enhance the level of exon 7-containing SMN2 mRNA in cells of the subject.

In any of the compositions or methods herein, the antisense oligonucleotide can comprise a Morpholino backbone.

BRIEF DESCRIPTION OF THE DRAWINGS

FIG. 2 is a sequence alignment showing the sequences of SEQ ID NOs: 6-18 (bold and underlined nucleotides of v1.00-v1.12, respectively) complementary to the SMN2 pre-mRNA-133 to −46 region upstream of intron 7. The full sequences of v1.00-v1.12 correspond to SEQ ID NOs: 33-45, respectively.

FIG. 18a shows the percent weight gained from birth to peak was also compared between groups treated in Example 3.

FIG. 18b shows statistical significance between each treatment group in FIG. 18a.

FIG. 24b shows Western blot quantification of FIG. 24a.

DESCRIPTION OF THE SEQUENCES

Figure 1:
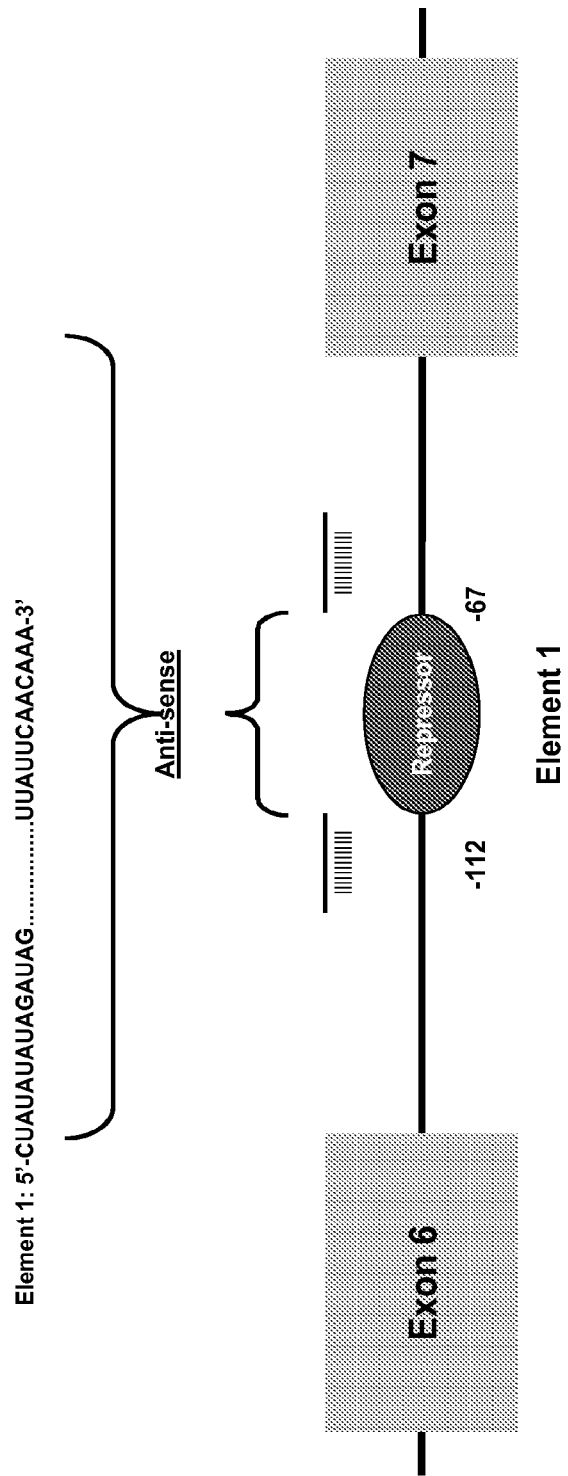
FIG. 1 is a schematic illustration of the location of Element 1 relative to Exon 7 of the SMN2 pre-mRNA and an exemplary antisense oligonucleotide according to one embodiment of the invention. 5'-CUAUAUAUAGAUAG (SEQ ID NO: 25), UUAUUCAACAAA-3' (SEQ ID NO: 26).

Illustrative examples of sequences useful in certain embodiments of the invention, including antisense oligo sequences targeting the E1 repressor include, but are not limited to, the following:

1. SEQ ID NO: 1 is a partial Intron 6 sequence
containing the entire Element 1 (-112; -67):
                                        (SEQ ID NO: 1)
5'-TGCAAGAAAACCTTAACTGCAGCCTAATAATTGTTTTCTTTGGGAT

AACTTTTAAAGTACATTAAAAGACTATCAACTTAATTTCTGATCATATT

TTGTTGAATAAAATAAGTAAAATGTCTTGTGAAACAAAATGCTTTTTAA

CATCCATATAAAGCTATCTATATATAGCTATCTATGTCTATATAGCTAT

TTTTTTTAACTTCCTTTATTTTCCTTACA [EXON7]-3'

2. SEQ ID NO: 2 is the Miaso 45-mer Element 1
(-112; -67) within Intron 6:
                                        (SEQ ID NO: 2)
5'-(112)GTAAAATGTCTTGTGAAACAAAATGCTTTTTAACATCCATA TAAA(67)-3'
(Miaso 45-mer; bold within SEQ ID NO: 1 above)

3. SEQ ID NO: 3 is a partial sequence of SEQ ID
NO: 1 comprising E1 flanking regions shown in
bold:
                                        (SEQ ID NO: 3)
5'-(134)ATATTTGTTGAATAAAATAAGTAAAATGTCTTGTGAAACA

AAATGCTTTTTAACATCCATATAAAGCTATCTATATATAGCTATCT

(54)-3'

4. SEQ ID NO: 4 is the reverse of SEQ ID NO: 3
(i.e, SEQ ID NO: 3 shown 3' to 5'):
                                        (SEQ ID NO: 4)
3'-TCTATCGATATATCTATCGAATATACCTACATTTTTCGTAACAA

GTGTTCTGTAAAATGAATAAAATAAGTTGTTTTATA-5'

5. SEQ ID NO: 5 is an ASO-based bifunctional
(BiF) RNA targeting the E1 repressor:
                                        (SEQ ID NO: 5)
5'-CTATATATAGATAGTTATTCAACAAAACTAGTAATTTTT-3'

6. SEQ ID NO: 6 is a 26-mer antisense sequence
targeting the E1 repressor referred to herein as
"Element 1 v1.00 ASO":
                                        (SEQ ID NO: 6; v1.00)
5'-CTATATATAGATAGTTATTCAACAAA-3'

7. SEQ ID NO: 7 is a 25-mer antisense sequence
targeting the E1 repressor referred to herein as
"Element 1 v1.01 ASO":
                                        (SEQ ID NO: 7; v1.01)
5'-TAGATAGCTTTACATTTTACTTATT-3'

8. SEQ ID NO: 8 is a 25-mer antisense sequence
targeting the E1 repressor referred to herein as
"Element 1 v1.02 ASO":
                                        (SEQ ID NO: 8; v1.02)
5'-TATGGATGTTAAAAAGCATTTTGTT-3'

9. SEQ ID NO: 9 is a 25-mer antisense sequence
targeting the E1 repressor referred to herein as
"Element 1 v1.03 ASO":
                                        (SEQ ID NO: 9; v1.03)
5'-CTATATATAGATAGCTTTATATGGA-3'

10. SEQ ID NO: 10 is a 25-mer antisense sequence
targeting the E1 repressor referred to herein as
"Element 1 v1.04 ASO":
                                        (SEQ ID NO: 10; v1.04)
5'-CATTTTACTTATTTTATTCAACAAA-3'

11. SEQ ID NO: 11 is a 25-mer antisense sequence
targeting the E1 repressor referred to herein as
"Element 1 v1.05 ASO":
                                        (SEQ ID NO: 11; v1.05)
5'-GCTTTATATGGACATTTTACTTATT-3'

12. SEQ ID NO: 12 is a 25-mer antisense sequence
targeting the E1 repressor referred to herein as
"Element 1 v1.06 ASO":
                                        (SEQ ID NO: 12; v1.06)
5'-GATGTTAAAAAGCGTTTCACAAGAC-3'

-continued

13. SEQ ID NO: 13 is a 25-mer antisense sequence targeting the E1 repressor referred to herein as "Element 1 v1.07 ASO":

(SEQ ID NO: 13; v1.07)
5'-TATATGGATGTTATTATTCAACAAA-3'

14. SEQ ID NO: 14 is a 25-mer antisense sequence targeting the E1 repressor referred to herein as "Element 1 v1.08 ASO":

(SEQ ID NO: 14; v1.08)
5'-GCATTTTGTTTCACAAGTTATTCAA-3'

15. SEQ ID NO: 15 is a 25-mer antisense sequence targeting the E1 repressor referred to herein as "Element 1 v1.09 ASO":

(SEQ ID NO: 15; v1.09)
5'-CTATATATAGATAGCGACATTTTAC-3'

16. SEQ ID NO: 16 is a 26-mer antisense sequence targeting the E1 repressor referred to herein as "Element 1 v1.10 ASO":

(SEQ ID NO: 16; v1.10)
5'-AGATAGCTTTATATGGATTTATTCAA-3'

17. SEQ ID NO: 17 is a 20-mer antisense sequence targeting the E1 repressor referred to herein as "Element 1 v1.11 ASO":

(SEQ ID NO: 17; v1.11)
5'-CTATATATAGTTATTCAACA-3'

18. SEQ ID NO: 18 is a 24-mer antisense sequence targeting the E1 repressor referred to herein as "Element 1 v1.12 ASO":

(SEQ ID NO: 18; v1.12)
5'-TTTATATGGATGAAGACATTTTAC-3'

19. SEQ ID NO: 19 is a mSmn-WT forward primer:

(SEQ ID NO: 19)
5'-tctgtgttcgtgcgtggtgactttt-3'

20. SEQ ID NO: 20 is a mSmn-WT reverse primer:

(SEQ ID NO: 20)
5'-cccaccacctaagaaagcctcaat-3'

21. SEQ ID NO: 21 is a Smn knockout SMN1-KO forward primer:

(SEQ ID NO: 21)
5'-ccaacttaatcgccttgcagcaca-3'

22. SEQ ID NO: 22 is a Smn knockout SMN1-KO reverse primer:

(SEQ ID NO: 22)
5'-aagcgagtggcaacatggaaatcg-3'

23. SEQ ID NO: 23 is a negative scrambled control:

(SEQ ID NO: 23)
5'-CCU CUU ACC UCA GUU ACA AUU UAU A-3'

24. SEQ ID NO: 24 is a E1$^{MO}$-ASO (26-mer):

(SEQ ID NO: 24)
5'-CUA UAU AUA GAU AGU UAU UCA ACA AA-3'

DETAILED DESCRIPTION

Spinal muscular atrophy (SMA) is a neurodegenerative disease caused by the loss of Survival Motor Neuron-1 (SMN1) (SMN1=survival of motor neuron 1, telomeric [*Homo sapiens*] GenBank accession number NG_008691.1 (Genomic); NC_000005.10 (Chromosome); NM_000344.3→NP_000335.1 (mRNA & Protein)). In all SMA patients a nearly identical copy gene called SMN2 is present which produces low levels of functional protein due to an alternative splicing event (SMN2=survival of motor neuron 2, centromeric [*Homo sapiens*] GenBank accession number NG_008728.1 (Genomic); NC_000005.10 (Chromosome); NM_017411.3→NP_059107.1 (mRNA & Protein)).

Without being bound by theory, certain aspects of the invention are drawn to preventing exon-skipping by targeting an intronic repressor, SMN2 Element 1 (E1), located upstream (5'-) of SMN2 exon 7 (FIG. 1). In certain embodiments, E1 and/or regions upstream (5'-) and/or downstream (3'-) of E1 are targeted using compositions comprising antisense-oligonucleotides (referred to herein generally as E1-ASOs) (illustrative examples shown in FIG. 2). Certain embodiments are drawn to compositions for blocking or inhibiting the repressive activity of the Element E1 of the SMN2 pre-mRNA wherein the composition comprises an antisense oligonucleotide. It is understood that a composition comprising an antisense oligonucleotide could consist or essentially consist of an antisense oligonucleotide such that certain embodiments are drawn to antisense oligonucleotides for blocking or inhibiting the repressive activity of the Element E1 of the SMN2 pre-mRNA. As used herein, "blocking" or "inhibiting" is used to describe the process of limiting and/or preventing the repressor function of SMN2 Element 1. In certain embodiments, any of the antisense oligonucleotides described herein are Morpholino-based antisense oligonucleotides (referred to herein generally as E1$^{MO}$-ASOs). Morpholino oligonucleotides, as referred to herein, comprise morpholine rings in their backbones, which replace the ribose or deoxyribose rings characteristic of RNA and DNA oligonucleotides. Morpholinos contain uncharged phosphorodiamidate inter-subunit linkages instead of the anionic phosphodiester linkage found in natural nucleic acids. The morpholine rings carry A, C, G or T bases positioned suitably for Watson-Crick base pairing.

SMN2 Element 1 (E1) has been previously explored by characterizing the genetic region upstream of SMN2 exon 7 as a repressor of SMN2 exon 7 inclusion. The genetic activity of E1 reduces the production of the full-length SMN product by promoting the exclusion of exon 7 and the expression of the truncated isoform (SMN-delta 7). 2'-O-Methyl ASO-based bifunctional (BiF) RNAs have been tested that target the E1 repressor and with ICV injection extended survival by ~48 hours. BiF RNAs are ASO-like molecules that derive their name from the presence of two functional domains: an RNA sequence that is an antisense element complementary to a specific cellular RNA (e.g. SMN Intron 6, Exon 7, or Intron 7); and an untethered RNA segment that serves as a sequence-specific binding platform for cellular splicing factors, such as SR proteins. The 5' end of exon 7 was targeted with the antisense element; however, it is possible that an antisense sequence within exon 7 does not allow for proper recognition of the necessary splicing signals. To enhance the activity of the SMN bifunctional RNAs, a set of RNAs that targeted E1 and ISS-N1 were developed. By targeting a repressor sequence with the anti-sense sequence, there was a 2-fold mechanism of SMN induction: inhibition of the intronic repressor and recruitment of SR proteins via the SR recruitment sequence of the bifunctional RNA. Based upon molecular understanding of SMN exon 7 regulation, high affinity binding sites for hTra21 or SF2/ASF—two factors known to stimulate exon 7 inclusion were incorporated. However, the 2'-O-Methyl chemistry used in these experiments has proven to be suboptimal for in vivo activity.

Antisense oligonucleotides targeting the E1 region and/or surrounding regions of SMN2 (i.e., distinct from targeting ISS-N1) have been developed and examined in two important animal models of disease: the "gold standard" SMNΔ7 mouse, which is a very severe model living only ~14 days; and a recently developed model called SMN$^{RT}$, in which animals live ~35 days and represent a less severe population.

Work was done in transgenic mouse that has the human SMN2 gene. All data herein (e.g., RNA, protein, etc.) represent the human SMN2 gene in a mouse with the mouse Smn gene deleted (Smn1=survival motor neuron 1 [*Mus musculus* (house mouse)] GenBank accession number NT_187006.1 (Genomic); NC_000079.6 (Chromosome); NM_011420.2→NP_035550.1 survival motor neuron protein isoform 1 (mRNA & Protein) NM_001252629.1→NP_001239558.1 survival motor neuron protein isoform 2 (mRNA & Protein)). Therefore, in certain embodiments, antisense oligonucleotides are targeted to the human SMN2 gene.

It has been discovered that using a relatively low dose of certain Element 1 Morpholino ASOs (E1$^{MO}$-ASOs), the SMA phenotype at the molecular, cellular, and organismal levels were largely rescued, including a 300-700% extension in survival for the two mouse models. From a pre-clinical perspective, there is excellent target engagement (SMN2 splicing), molecular efficacy (SMN protein production), and robust phenotypic rescue in two complementary models of disease. Collectively, this work identifies lead ASO candidates that target a distinct region of the SMN2 pre-mRNA.

Representative embodiments of the invention are directed to new methods and compositions based on Antisense Oligonucleotides (ASOs) technology and Morpholino chemistry for modulating the SMN2 splicing pattern to generate increased levels of exon 7-containing full-length SMN. In certain embodiments, the increased level of exon 7-containing full-length SMA is sufficient to provide a viable therapy to Spinal Muscular Atrophy (SMA) patients. Certain embodiments comprise a series of compositions capable of blocking or inhibiting the repressive activity of the SMN2 splice silencing domain, Element 1 (E1). For example, certain embodiments comprise E1 antisense oligonucleotide based compositions that block or inhibit the splice inhibitory effects of the E1, thereby modulating splicing of the SMN2 pre-mRNA to generate exon 7 retaining full-length SMN.

In certain embodiments, a composition comprises an E1 antisense oligonucleotide (E1-ASO) with a sequence annealing to two distinct regions flanking E1 on the SMN2 pre-mRNA, wherein the regions comprise the nucleotides between −134 to −120 and −67 to −54 (relative to exon 7). In certain embodiments, such E1-ASO further comprises a Morpholino backbone.

FIG. 1 illustrates an exemplary E1-ASO. As shown in FIG. 1, the E1-ASO is designed with two split antisense sequences annealing to two regions flanking repressor E1: Region (67-54) and Region (134-120). To increase exon 7-containing SMN expression, a two-pronged strategy to design the antisense may be used: on one side includes two antisense regions that block E1 and on the other end a sequence that recruits exonic splice enhancers specific for exon 7.

Other embodiments can incorporate additional antisense oligonucleotides annealing to the sequences on either side of the two regions—i.e., Region (−67 to −54) and Region (−134 to −120)—and/or sequences within or partially within the E1 motif. FIG. 2 is an alignment (sequences shown reversed, i.e., 3' to 5') of the region comprising the nucleotides −46 to −133 that are 5' (upstream) of SMN2 Exon 7, including the E1 motif (italicized nucleotides), and showing in bold underline the sequences of the region of the SMN2 pre-mRNA complementary to the antisense oligonucleotide sequences of SEQ ID NOs: 6 to 18, i.e., v1.00 to v.1.12, respectively.

Certain embodiments are drawn to compositions comprising an antisense oligonucleotide that comprises a nucleotide sequence that anneals to the region comprising nucleotides −46 to −133 that are 5' (upstream) of SMN2 Exon 7. In certain embodiments, the antisense oligonucleotide comprises a sequence that anneals to two regions of the nucleotides −46 to −133 that are 5' (upstream) of SMN2 Exon 7, wherein the first region comprises the nucleotides between −134 to −90 relative to exon 7 of the SMN2 pre-mRNA and the second region comprises the nucleotides between −105 and −45 relative to exon 7 of the SMN2 pre-mRNA. In order for an antisense oligonucleotide targeting the E1 region to modulate the activity of Element 1, it is understood that "anneal(s)" or "annealing," as used herein, refers to annealing of two substantially complementary nucleic acid molecules under physiological conditions. In certain embodiments, the first region comprises: the nucleotides between −134 to −90; the nucleotides between −134 to −95; the nucleotides between −134 to −100; the nucleotides between −134 to −105; the nucleotides between −134 to −110; or the nucleotides between −134 to −115, relative to exon 7 of the SMN2 pre-mRNA. In certain embodiments, the second region comprises: the nucleotides between −90 to −45; the nucleotides between −85 to −45; the nucleotides between −80 to −45; the nucleotides between −75 to −45; the nucleotides between −70 to −45; or the nucleotides between −65 to −45, relative to exon 7 of the SMN2 pre-mRNA. In certain embodiments, the first and/or second regions consist of any of the above defined regions upstream of exon 7 of the SMN2 pre-mRNA. In certain embodiments the first and second regions of the SMN2 pre-mRNA are a combination of any of the above first and second regions, for example the first region comprises the nucleotides between −134 to −95 and the second region comprises the nucleotides between −85 to −45, for example the first region comprises the nucleotides between −134 to −115 and the second region comprises the nucleotides between −65 to −45, etc.

In certain embodiments, the antisense oligonucleotide sequence comprises a certain number of nucleotides that are complementary to consecutive nucleotides of the region comprising the nucleotides −46 to −133 that are 5' (upstream) of SMN2 Exon 7. In certain embodiments, the antisense oligonucleotide comprises a nucleotide sequence that is complementary to at least 6, 7, 8, 9, 10, 11, 12, 13, 14, 15, 16, 17, 18, 19, 20, 21, 22, 23, 24, 25, or 26 consecutive nucleotides of the region comprising nucleotides −46 to −133 that are 5' (upstream) of SMN2 Exon 7. In certain embodiments, the antisense oligonucleotide comprising a nucleotide sequence that is complementary to at least 6, 7, 8, 9, 10, 11, 12, 13, 14, 15, 16, 17, 18, 19, 20, 21, 22, 23, 24, 25, or 26 consecutive nucleotides of the region comprising nucleotides −46 to −133 that are 5' (upstream) of SMN2 Exon 7 is not entirely complementary and comprises one, two, three, four, five, or six nucleotide substitutions in the antisense oligonucleotide sequence. In certain embodiments, the antisense oligonucleotide comprises a nucleotide sequence that is complementary to at least 6, 7, 8, 9, 10, 11, 12, 13, 14, or 15 consecutive nucleotides of any of the first regions listed herein. In certain embodiments, the antisense oligonucleotide comprising a nucleotide sequence that is complementary to at least 6, 7, 8, 9, 10, 11, 12, 13, 14, or 15 consecutive nucleotides of any of the first regions listed herein is not entirely complementary and comprises one, two, three, four, five, or six, nucleotide substitutions in the antisense oligonucleotide sequence. In certain embodiments, the antisense oligonucleotide comprises a nucleotide sequence that is complementary to at least 6, 7, 8, 9, 10, 11, 12, 13, 14, or 15 consecutive nucleotides of any of the second regions listed herein. In certain embodiments, the antisense oligonucleotide comprising a nucleotide sequence that is complementary to at least 6, 7, 8, 9, 10, 11, 12, 13, 14, or 15 consecutive nucleotides of any of the second regions listed herein is not entirely complementary and comprises one, two, three, four, five, or six, nucleotide substitutions in the antisense oligonucleotide sequence. In certain embodiments, the antisense oligonucleotide comprises a nucleotide sequence that is complementary to at least 6, 7, 8, 9, 10, 11, 12, 13, 14, or 15 consecutive nucleotides of any of the first regions listed herein and complementary to at least 6, 7, 8, 9, 10, 11, 12, 13, 14, or 15 consecutive nucleotides of any of the second regions listed herein. In certain embodiments, the antisense oligonucleotide comprising a nucleotide sequence that is complementary to at least 6, 7, 8, 9, 10, 11, 12, 13, 14, or 15 consecutive nucleotides of any of the first regions listed herein and complementary to at least 6, 7, 8, 9, 10, 11, 12, 13, 14, or 15 consecutive nucleotides of any of the second regions listed herein is not entirely complementary and comprises one, two, three, four, five, or six, nucleotide substitutions in the antisense oligonucleotide sequence. In certain embodiments, the antisense oligonucleotide comprises a nucleotide sequence that is complementary to at least eight consecutive nucleotides of any of the first regions listed herein. In certain embodiments, the antisense oligonucleotide comprises a nucleotide sequence that is complementary to at least eight consecutive nucleotides of any of the second regions listed herein. In certain embodiments, the antisense oligonucleotide comprises a nucleotide sequence that is complementary to at least eight consecutive nucleotides of any of the first regions listed herein and complementary to at least eight consecutive nucleotides of any of the second regions listed herein. In the SMN2 pre-mRNA, the first regions listed herein are upstream (5') of the second regions listed herein. In the antisense oligonucleotide sequences, however, the nucleotide sequence of the antisense oligonucleotide that is complementary to the second region of the SMN2 pre-mRNA is upstream (5') of the nucleotide sequence of the antisense oligonucleotide that is complementary to the first region of the SMN2 pre-mRNA.

Certain embodiments are drawn to compositions comprising an antisense oligonucleotide that comprises a nucleotide sequence that anneals to the region consisting of nucleotides −46 to −133 that are 5' (upstream) of SMN2 Exon 7. In certain embodiments, the antisense oligonucleotide comprises a sequence that anneals to two regions of the nucleotides −46 to −133 that are 5' (upstream) of SMN2 Exon 7, wherein the first region consists of the nucleotides between −134 to −90 relative to exon 7 of the SMN2 pre-mRNA and the second region consists of the nucleotides between −105 and −45 relative to exon 7 of the SMN2 pre-mRNA. In order for an antisense oligonucleotide targeting the E1 region to modulate the activity of Element 1, it is understood that "anneal(s)" or "annealing," as used herein, refers to annealing of two substantially complementary nucleic acid molecules under physiological conditions. In certain embodiments, the first region consists of: the nucleotides between −134 to −90; the nucleotides between −134 to −95; the nucleotides between −134 to −100; the nucleotides between −134 to −105; the nucleotides between −134 to −110; or the nucleotides between −134 to −115, relative to exon 7 of the SMN2 pre-mRNA. In certain embodiments, the second region consists of: the nucleotides between −90 to −45; the nucleotides between −85 to −45; the nucleotides between −80 to −45; the nucleotides between −75 to −45; the nucleotides between −70 to −45; or the nucleotides between −65 to −45, relative to exon 7 of the SMN2 pre-mRNA. In certain embodiments, the first and/or second regions consist of any of the above defined regions upstream of exon 7 of the SMN2 pre-mRNA. In certain embodiments the first and second regions of the SMN2 pre-mRNA are a combination of any of the above first and second regions, for example the first region consists of the nucleotides between −134 to −95 and the second region consists of the nucleotides between −85 to −45, for example the first region consists of the nucleotides between −134 to −115 and the second region consists of the nucleotides between −65 to −45, etc.

In certain embodiments, the antisense oligonucleotide sequence comprises a certain number of nucleotides that are complementary to consecutive nucleotides of the region consisting of the nucleotides −46 to −133 that are 5' (upstream) of SMN2 Exon 7. In certain embodiments, the antisense oligonucleotide comprises a nucleotide sequence that is complementary to at least 6, 7, 8, 9, 10, 11, 12, 13, 14, 15, 16, 17, 18, 19, 20, 21, 22, 23, 24, 25, or 26 consecutive nucleotides of the region consisting of nucleotides −46 to −133 that are 5' (upstream) of SMN2 Exon 7. In certain embodiments, the antisense oligonucleotide comprising a nucleotide sequence that is complementary to at least 6, 7, 8, 9, 10, 11, 12, 13, 14, 15, 16, 17, 18, 19, 20, 21, 22, 23, 24, 25, or 26 consecutive nucleotides of the region consisting of nucleotides −46 to −133 that are 5' (upstream) of SMN2 Exon 7 is not entirely complementary and comprises one, two, three, four, five, or six nucleotide substitutions in the antisense oligonucleotide sequence. In certain embodiments, the antisense oligonucleotide comprising a nucleotide sequence that is complementary to at least 6, 7, 8, 9, 10, 11, 12, 13, 14, or 15 consecutive nucleotides of any of the first regions listed herein. In certain embodiments, the antisense oligonucleotide comprising a nucleotide sequence that is complementary to at least 6, 7, 8, 9, 10, 11, 12, 13, 14, or 15 consecutive nucleotides of any of the first regions listed herein is not entirely complementary and comprises one, two, three, four, five, or six, nucleotide substitutions in the antisense oligonucleotide sequence. In certain embodiments, the antisense oligonucleotide comprises a nucleotide sequence that is complementary to at least 6, 7, 8, 9, 10, 11, 12, 13, 14, or 15 consecutive nucleotides of any of the second regions listed herein. In certain embodiments, the antisense oligonucleotide comprising a nucleotide sequence that is complementary to at least 6, 7, 8, 9, 10, 11, 12, 13, 14, or 15 consecutive nucleotides of any of the second regions listed herein is not entirely complementary and comprises one, two, three, four, five, or six, nucleotide substitutions in the antisense oligonucleotide sequence. In certain embodiments, the antisense oligonucleotide comprises a nucleotide sequence that is complementary to at least 6, 7, 8, 9, 10, 11, 12, 13, 14, or 15 consecutive nucleotides of any of the first regions listed herein and complementary to at least 6, 7, 8, 9, 10, 11, 12, 13, 14, or 15 consecutive nucleotides of any of the second regions listed herein. In certain embodiments, the antisense oligonucleotide comprising a nucleotide sequence that is complementary to at least 6, 7, 8, 9, 10, 11, 12, 13, 14, or 15 consecutive nucleotides of any of the first regions listed herein and complementary to at least 6, 7, 8, 9, 10, 11, 12, 13, 14, or 15 consecutive nucleotides of any of the second regions listed herein is not entirely complementary and comprises one, two, three, four, five, or six, nucleotide substitutions in the antisense oligonucleotide sequence. In certain embodiments, the antisense oligonucleotide comprises a nucleotide sequence that is complementary to at least eight consecutive nucleotides of any of the first regions listed herein. In certain embodiments, the antisense oligonucleotide comprises a nucleotide sequence that is complementary to at least eight consecutive nucleotides of any of the second regions listed herein. In certain embodiments, the antisense oligonucleotide comprises a nucleotide sequence that is complementary to at least eight consecutive nucleotides of any of the first regions listed herein and complementary to at least eight consecutive nucleotides of any of the second regions listed herein. In the SMN2 pre-mRNA, the first regions listed herein are upstream (5') of the second regions listed herein. In the antisense oligonucleotide sequences, however, the nucleotide sequence of the antisense oligonucleotide that is complementary to the second region of the SMN2 pre-mRNA is upstream (5') of the nucleotide sequence of the antisense oligonucleotide that is complementary to the first region of the SMN2 pre-mRNA.

In certain embodiments, while the antisense oligonucleotide anneals to and/or comprises a nucleotide sequence that is complementary to a first region and a second region upstream of exon 7 of the SMN2 pre-mRNA the antisense oligonucleotide sequence is non-sequential, there is a portion of the sequence of the SMN2 pre-mRNA that intervenes between the sequences of the SMN2 pre-mRNA to which the antisense oligonucleotide anneals or is complementary to. That is, the entire sequence of the antisense oligonucleotide is not complementary to a wholly consecutive sequence of the SMN2 pre-mRNA sequence. This is illustrated in FIG. 2, where the entire sequences of v1.00, v1.01, v1.05, v1.06, v1.07, v1.08, v.1.09, v1.10, v1.11, and v1.12 (corresponding to SEQ ID NOs: 6, and 11-18), are non-sequential with respect to the SMN2 pre-mRNA, that is split by intervening sequences of the SMN2 pre-mRNA.

Certain embodiments are drawn to compositions comprising an antisense oligonucleotide wherein the antisense oligonucleotide comprises, or in certain embodiments consists of, a nucleic acid sequence of SEQ ID NO: 6 (v1.00), SEQ ID NO: 7 (v1.01), SEQ ID NO: 8 (v1.02), SEQ ID NO: 9 (v1.03), SEQ ID NO: 10 (v1.04), SEQ ID NO: 11 (v1.05), SEQ ID NO: 12 (v1.06), SEQ ID NO: 13 (v1.07), SEQ ID NO: 14 (v1.08), SEQ ID NO: 15 (v1.09), SEQ ID NO: 16 (v1.10), SEQ ID NO: 17 (v1.11), and SEQ ID NO: 18 (v1.12). In certain embodiments, the antisense oligonucleotide sequence comprises, or in certain embodiments consists of, a nucleic acid sequence comprising one, two, three, four, five, or six nucleotide substitutions in the nucleotide sequence of any of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, and SEQ ID NO: 18.

In certain embodiments, any of the antisense oligonucleotides disclosed herein can be a modified nucleotide, such as a Morpholino antisense oligonucleotide.

Certain embodiments provide for methods of blocking the repressive activity of the Element 1 of the SMN2 pre-mRNA wherein the method comprises administrating to a subject a composition of the invention. Certain embodiments provide for methods of treating a SMA subject. In certain embodiments, the method comprises the step of administering to a subject an E1-ASO of an embodiment of the invention. The ability to block or inhibit the repressive activity of the Element 1 of the SMN2 pre-mRNA by an antisense oligonucleotide of the invention is does dependent. In certain embodiments, the E1-ASO is administered in a dose effective manner to enhance the level of exon 7-containing SMN2 mRNA in cells of the subject. In certain embodiments, the E1-ASO is administered in an effective amount to treat SMA in a patient. In certain embodiments, the patient is a mammal, such as a human. In certain embodiments, the E1-ASO is a Mopholino modified E1 ASO. One of ordinary skill in the art would understand that antisense oligonucleotides such as those described herein, including Morpholino modified nucleic acids, are commercially synthesized and/or otherwise produced by known methods. Intracerebroventricular (ICV), intraperitoneal (IP), and intravenous (IV) administration have been shown to result in increases in SMN protein. Combinatorial injections have proven to be the most efficacious. Thus, in certain embodiments, E1 ASOs can be administered via ICV, IP, IV, or a combinatorial administration thereof into a subject. In certain embodiments, an antisense oligonucleotide of the invention is administered via a 1 µM, 2 µM, 3 µM, 4 µM, or 5 µM ICV injection. In certain methods, a doubling dose is achieved via two ICV injections or an ICV+IP dosing.

In certain embodiments, the subject is a mammal. In certain embodiments, the subject is a human. In certain embodiments, the subject is a rodent such as a mouse or rat, for example, a transgenic mouse such as strain SMAΔ7 and "readthrough" mice (severe and intermediate forms of SMA). For example, following treatment, SMA mice showed significant weight gain, ambulated at near normal levels, lived 200 to 600% longer, and exhibited near-wild type levels of full-length (exon 7 retaining) SMN protein.

The following disclosed embodiments are merely representative of the invention which may be embodied in various forms. Thus, specific structural, functional, and procedural details disclosed in the following Examples are not to be interpreted as limiting.

EXAMPLES

Example 1

Figure 3:
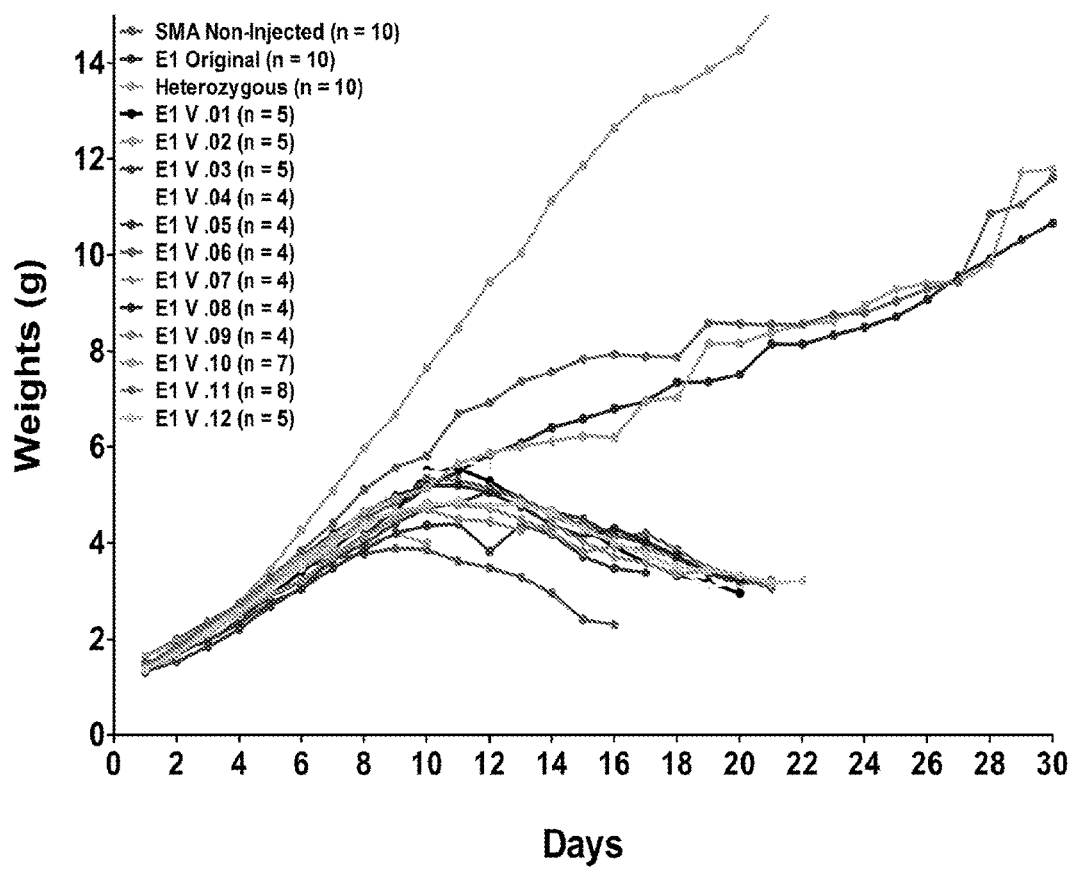
FIG. 3 shows weight gains among treated mice and controls in Example 1.

FIG. 3 shows the results of weight gain for SMA mice versus controls wherein the mice were injected with Morpholino antisense oligonucleotides comprising the nucleotide sequences of SEQ ID NOs: 6-18 (E1 V.00 (original) and E1 V.01 to V.12, respectively).

Figure 4:
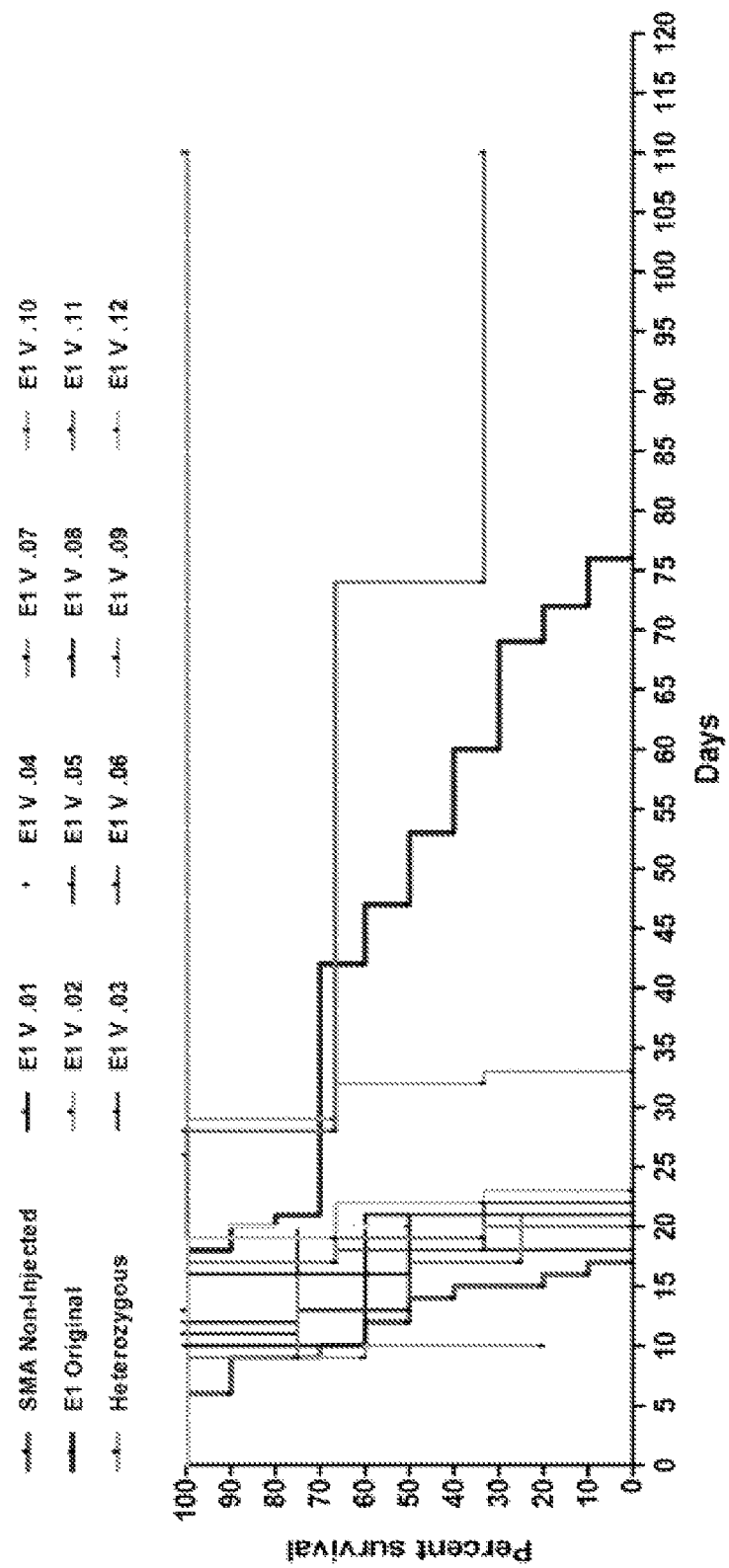
FIG. 4 shows survival among treated mice and controls in Example 1.

FIG. 4 shows the results of survival for SMA mice versus controls wherein the mice were injected with Morpholino antisense oligonucleotides comprising the nucleotide sequences of SEQ ID NOs: 6-18 (E1 V.00 (original) and V.01 to V.12, respectively).

Example 2

Figure 5:
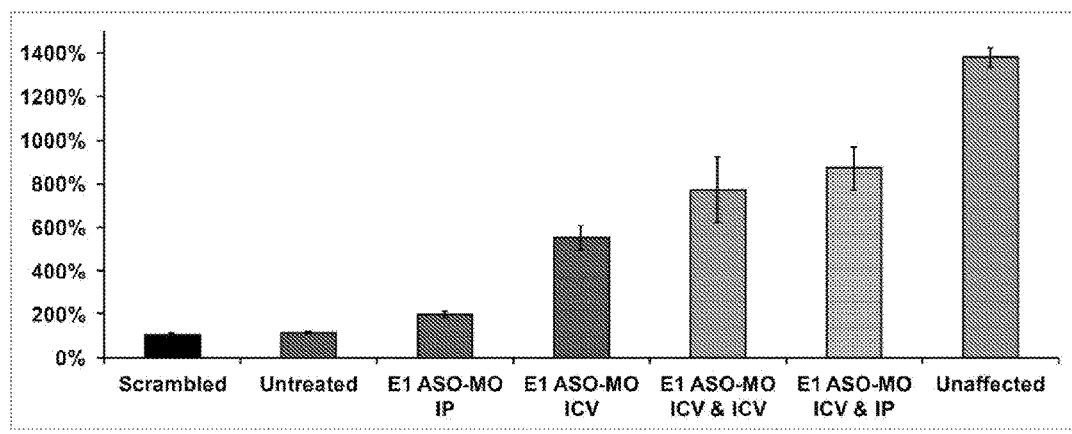
FIG. 5 is a bar graph summarizing the weight gains among treated mice and controls in Example 2.

FIG. 5 shows weight gains among $E1^{MO}$-ASO-v1.00-treated mice (severe form) and controls, showing the weight gained from birth to when a peak weight was reached. There were three control groups as well: 1) Animals injected with scrambled MO-ASOs (no binding specificity); 2) Unaffected healthy animals (heterozygous); and 3) Untreated SMA animals. As the data shows, IP injection had a slight improvement effect on weight gain, however, ICV injection alone had a much more significant impact on weight gain. Moreover, when a combination of both types of injections was used, the weight gain for the treated animals reaches almost 900% of their initial birth weight. Statistical calculations show the significance in the Table 1:

TABLE 1

| Treatment | Avg Weights | Std Deviation | Std Error | P value E1 Morph ICV | P value Untreated | P value Scrambled |
|---|---|---|---|---|---|---|
| Scrambled | 104% | 0.351 | 0.101 | 0.00001072 | 0.40907992 | 1.00000000 |
| Untreated | 115% | 0.233 | 0.067 | 0.00001517 | 1.00000000 | 0.40907992 |
| E1 Morph IP Only | 197% | 0.265 | 0.119 | 0.01520258 | 0.00001147 | 0.00009196 |
| E1 Morph ICV Only | 551% | 3.031 | 0.553 | 1.00000000 | 0.00001517 | 0.00000964 |
| E1 Morph ICV & IP | 874% | 4.412 | 1.103 | 0.00343686 | 0.00000061 | 0.00000050 |
| Heterozygous | 1380% | 1.520 | 0.439 | 0.00000000 | 0.00000000 | 0.00000000 |

Figure 6:
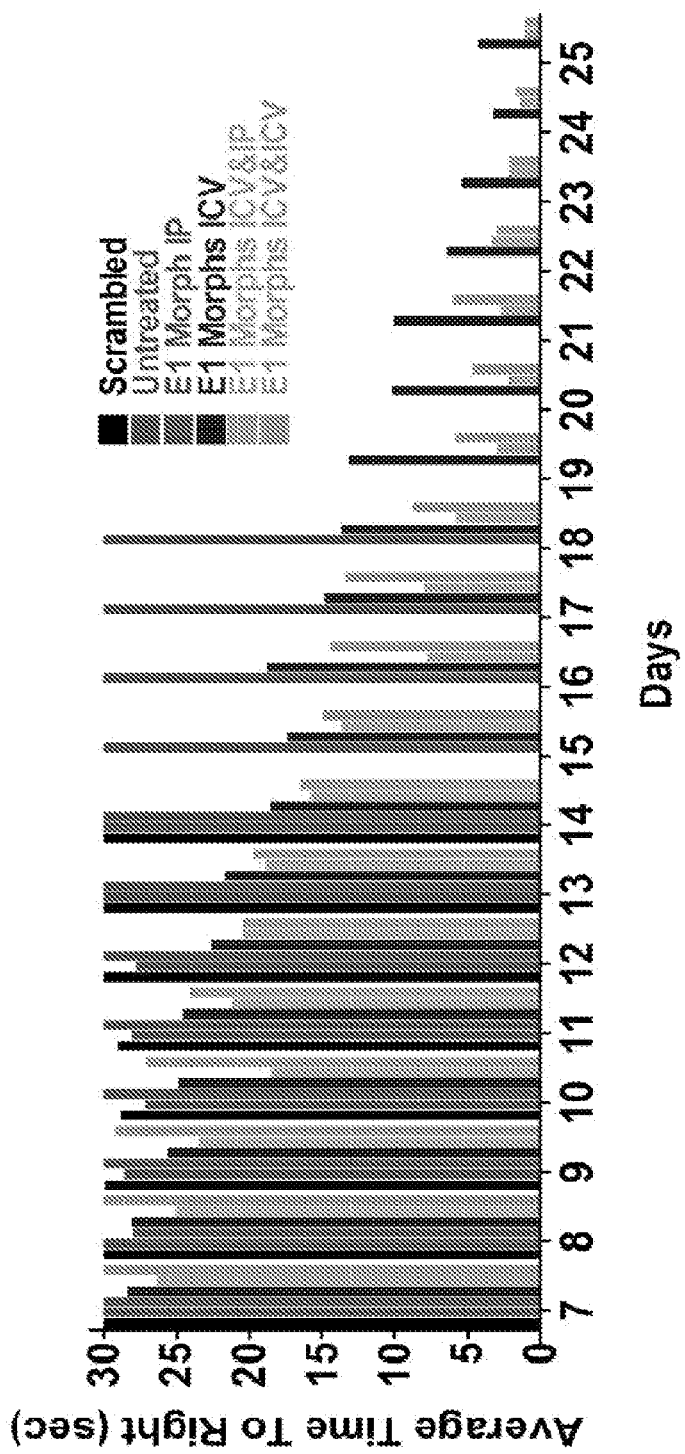
FIG. 6 is a bar graph summarizing the "Time to Right" motor function test among treated mice and controls in Example 2.

FIG. 6 shows the average times taken for animals (treated mice (severe form) and controls) to right themselves. Righting reflex is a motor function test performed on animals. Time-To-Right has been previously shown to be a sensitive measurement of gross motor function for SMA animals. In short, animals are placed on their backs and the time required to turn upright is measured. Animals that failed to turn in 30 seconds are considered failing the test. As shown in FIG. 6, measurements are from day 7 through 25. Healthy (heterozygous) animals can do this test within 1-5 seconds from day 7 onward. Although the IP injected animals failed this motor function test, the ICV and also the ICV&IP combinatorial injections have an incredible impact on the motor functions on the tested animals. After two weeks the ICV injected animals righted themselves under 15 seconds and the ICV&IP injected animals did so under 10 seconds. By day 20 the ICV&IP injected animals were turning under 5 seconds.

Figure 7:
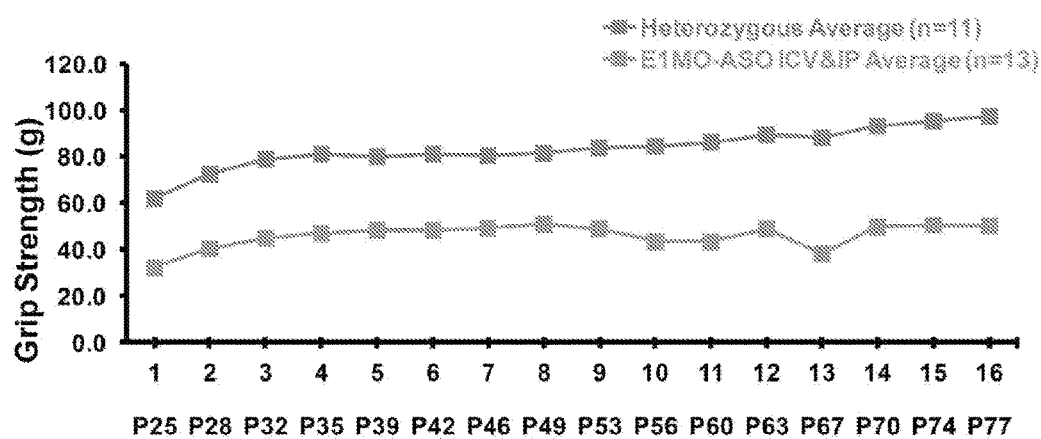
FIG. 7 is a graph summarizing the grip strength motor function test among treated mice and controls in Example 2.

FIG. 7 shows a comparison of grip strength between treated mice (severe form) and wild heterozygous mice. Grip strength is another motor function test to measure muscle functionality; the grip strength test is performed by placing animals on a device that measures the animal's pull (grip). The test compared the strength of the unaffected heterozygous mice and the MO-ASOs treated SMA animals after ICV&IP injections. 20 trials were measured on the days indicated from P25 to P91.

Figure 8:
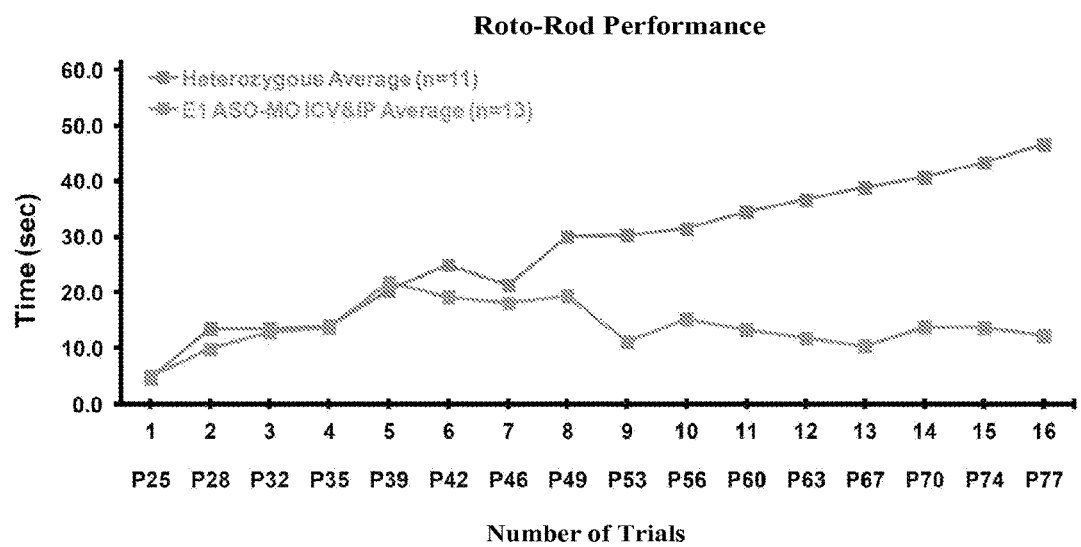
FIG. 8 is a graph summarizing the Rota-rod performance test between treated mice and the wild controls in Example 2.

FIG. 8 shows another performance test comparing treated mice and wild mice. In the Roto-Rod performance test, animals are placed on a rotating axle, while time is measured for their ability to stay on without falling. In the beginning, treated animals performed exactly like their healthy littermates. With time, their strength weakens and their performance decreases. Up until around day 45, treated animals performed virtually as unaffected heterozygous animals.

Figure 9:
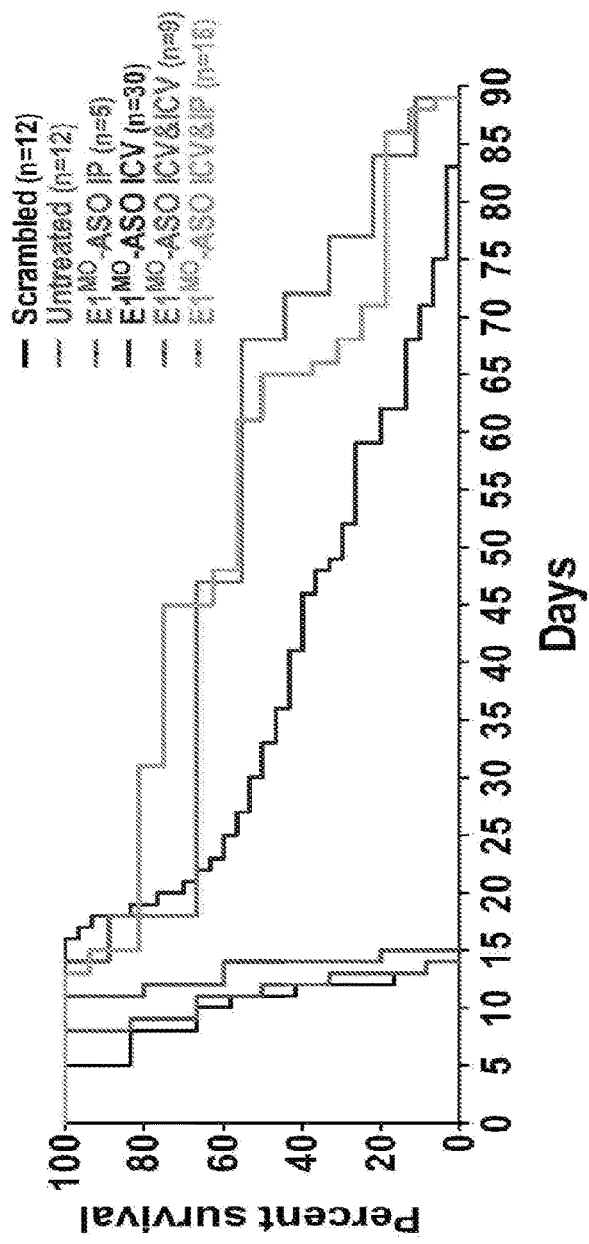
FIG. 9 is a graph summarizing the survival data among treated mice and various controls in Example 2.

FIG. 9 shows a comparison of the survival data among treated mice and controls. As shown in FIG. 9, the IP only injected animals had a very slight extension of survival. However, the ICV injected animals reached an average of 39 days (max. 83 days), whereas, the combinatorial ICV&IP injections extended the average life span to 54 days (max. 89 days). The extension of survival of the treated animals demonstrates the clinic potential of treatment based on ASOs targeting E1.

Figure 10:
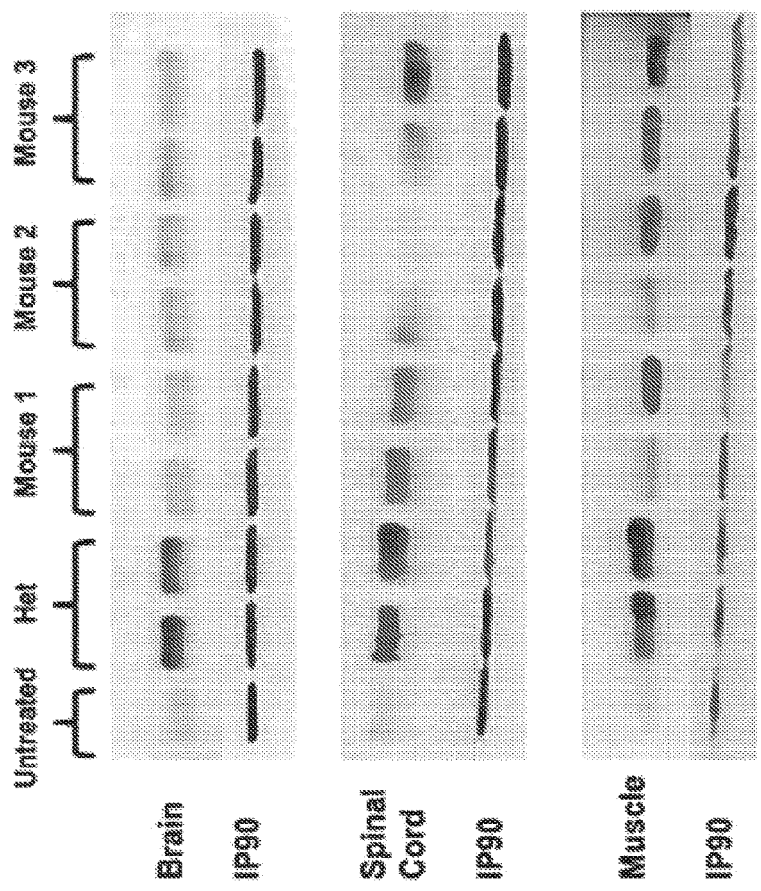
FIG. 10 is an array and Western Blot analysis on protein induction among the treated mice and controls in Example 2.

FIG. 10 shows Western-blot analysis to determine the SMN protein induction in treated animals (severe form with ICV injections only) compared to controls. Protein induction was significantly higher in all tissues tested with substantial increase in spinal cord and muscle tissues. Three separate mice were used to determine the significance in the protein induction.

Figure 11:
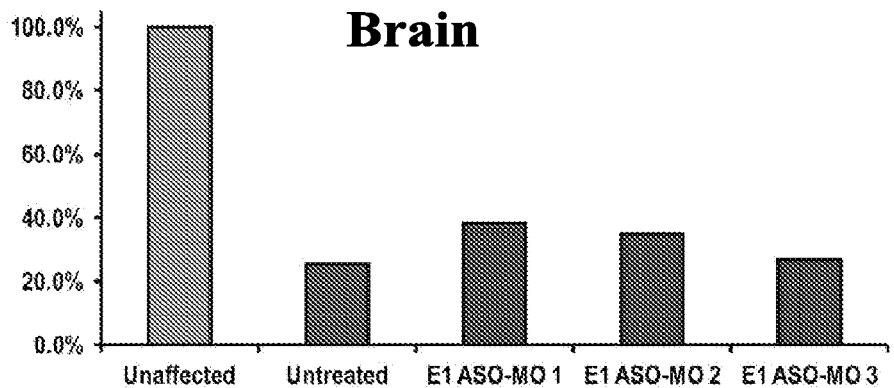
FIG. 11 is a quantitative graph for the Western Blot analysis in Example 2.
Figure 11:
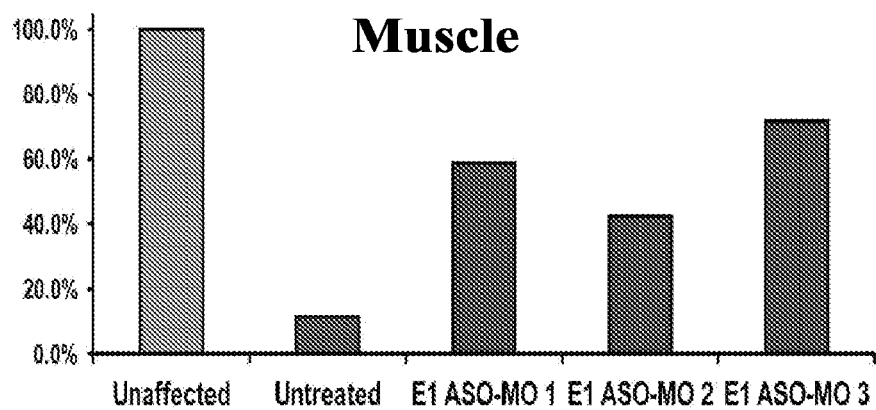
Figure 11:
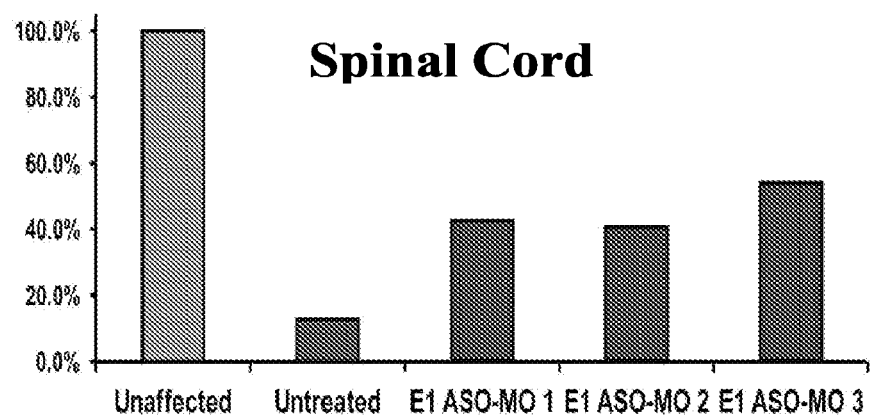

FIG. 11 shows protein induction in different types of tissue. As shown in FIG. 11, three quantification graphs of the Western Blots data further confirmed the significant increase in protein production especially in muscle and spinal cord tissues. The Western Blots analysis further proved the viability of the treatment based on the inventive ASOs targeting E1.

The same experimental and testing design was been applied to a different, intermediate mouse model (the "Readthrough" mice), representing a milder form of SMA, through the ICV injections only. The data on weight gain increases, various motor functionality tests, and average protein induction analysis was comparable to that of the treated severe-form mice.

Figure 12A:
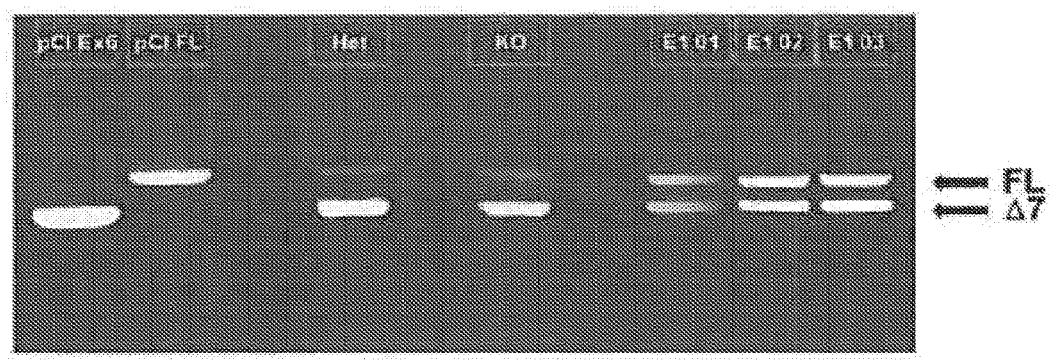
FIG. 12a shows the RT-PCR analysis for SMN-full length and SMNΔ7 levels in the cells of treated mice and controls in Example 2.
Figure 12B:
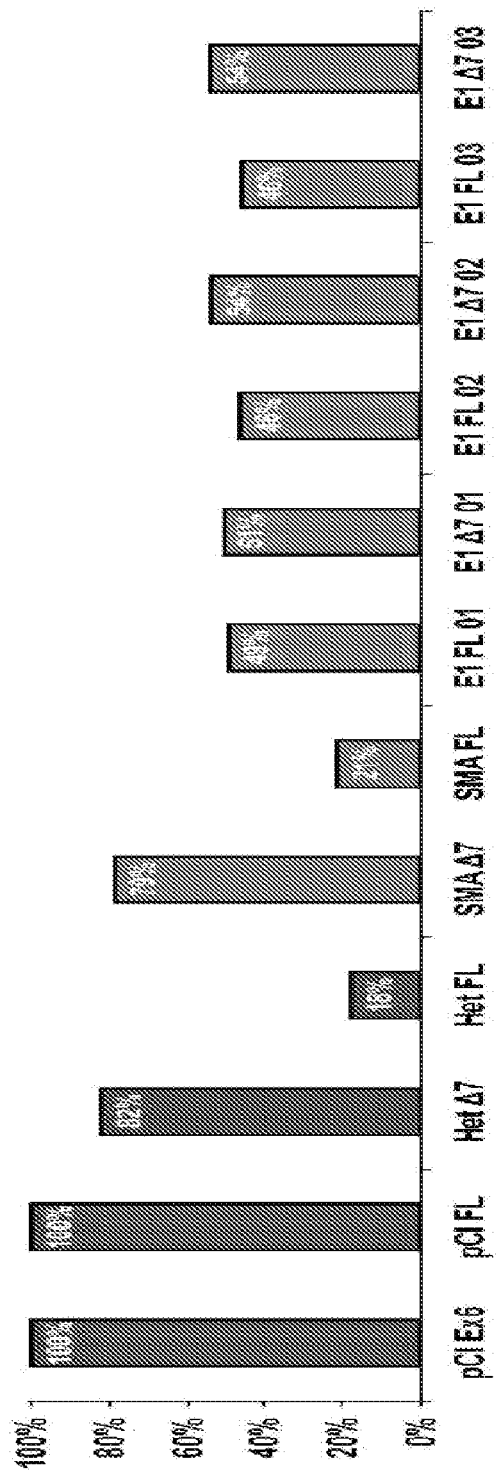
FIG. 12b is a quantitative graph for SMN-full length and SMNΔ7 levels in the cells of the treated mice and controls in Example 2.

FIG. 12(a,b) shows RT-PCR analysis for SMN-full length and SMNΔ7 on treated mice and controls. As shown in FIG. 12(a,b), the level of exon 7-retaining full length SMN increased significantly in the mice treated with the inventive Morpholino modified E1 ASOs.

Example 3

A single intracerebroventricular (ICV) injection of E1$^{MO}$-ASO (Element 1 v1.00; SEQ ID NO: 6) in the relatively severe mouse model of SMA (SMNΔ7 mouse model) elicited a robust induction of SMN protein and mean life span was extended ~300% following a single dose, consistent with large weight gains and a correction of the neuronal pathology. Additionally, E1$^{MO}$-ASO (Element 1 v1.00; SEQ ID NO: 6) treatment in an intermediate SMA mouse (SMN$^{RT}$ mouse model) significantly extended life span by nearly 700% and weight gain was comparable to the unaffected animals. While a number of experimental therapeutics have targeted the ISS-N1 element of SMN2 pre-mRNA, the development of E1 ASOs provides a new molecular target for SMA therapeutics that dramatically extends survival in two important pre-clinical models of disease.

Materials and Methods

Animal Procedures and ASO Delivery

Animals were housed and treated in accordance with Animal Care and Use Committee guidelines of the University of Missouri, Columbia, Mo., USA. The colony was maintained as heterozygote breeding pairs under specific pathogen free conditions. SMNΔ7 (SMNΔ7$^{+/+}$; SMN2$^{+/+}$; Smn$^{-/-}$) and SMN$^{RT}$ (SMN$^{RT+}$; SMN2$^{+/+}$; Smn$^{-/-}$) mice were genotyped on the day of birth (P1) using standard PCR protocol (JAX® Mice Resources) on tail tissue material. The following primer sets were used: for the mouse Smn gene, mSmn-WT forward (5'-tctgtgttcgtgcgtggtgactttt-3') (SEQ ID NO: 19) and mSmn-WT reverse (5'-cccaccacctaagaaagcctcaat-3') (SEQ ID NO: 20) and for the Smn knockout SMN1-KO forward (5'-ccaacttaatcgccttgcagcaca-3') (SEQ ID NO: 21) and SMN1-KO reverse (5'-aagcgagtggcaacatggaaatcg-3') (SEQ ID NO: 22). ICV injections were performed on P2, as previously described (Coady, T. H., et al., 2008; Osman, E. Y., et al., 2012; Passini, M. A., et al., 2011).

Mice were immobilized via cryoanesthesia and injected using μL calibrated sterilized glass micropipettes. The injection site was approximately 0.25 mm lateral to the sagittal suture and 0.50-0.75 mm rostral to the neonatal coronary suture. The needles were inserted perpendicular to the skull surface using a fiber-optic light (Boyce Scientific Inc.) to aid in illuminating pertinent anatomical structures. Needles were removed after 10 seconds of discontinuation of plunger movement to prevent backflow. Treated animals were placed in a warmed container for recovery (5-10 minutes) until movement was restored. Single injections of 2 μL of the Morpholino modified $E1^{MO}$-ASOs were delivered via intracerebroventricular injections (ICV) as described above for all mice. Time-to-right (TTR) reflex tests were conducted as previously described (Butchbach, M. E., et al., 2007). Each pup was placed onto its back and the time it takes to right itself on the ground was recorded. The test was terminated at 30 seconds and if an animal had not turned by this time, it was recorded as 'Failure'. Righting reflex measurement were recorded daily starting at P7 since unaffected animals start to turn over at this time. For grip strength assessment, a grasping response test was utilized. Each pup's front paws were placed on a wire mesh (1 cm² grids) and gently dragged horizontally along the mesh (BioSeb Model BP32025, Vitrolles, FR, EU & Pinellas Park, Fla., USA). Any resistance felt was scored as a positive response. The strength of the animal holding onto the mesh before release was recorded in grams. Grip strength was measured every 3-4 days starting on P25. Motor activity and coordination were measured by utilizing rotarod treadmill for mice (IITC Rotarod Series 8, IITC Life Science Inc., CA, USA). The animals were placed on textured drums to avoid slipping. When the tested animal dropped onto the individual sensing platform below, the test results were recorded in seconds. Measurements were performed every 3-4 days starting on P25.

Element 1 Antisense Oligonucleotides v1.00 ($E1^{MO}$-ASO v1.00)

The following oligos were modified at every base with Morpholino chemistry groups (GeneTools L.L.C., Philomath, Oreg. 97370 USA); $E1^{MO}$-ASO (26-mer) 5'-CUA UAU AUA GAU AGU UAU UCA ACA AA-3' (SEQ ID NO: 23), and negative scrambled control provided and tested by GeneTools L.L.C. (25-mer), 5'-CCU CUU ACC UCA GUU ACA AUU UAU A-3' (SEQ ID NO: 24).

Immunohistochemistry of Neuromuscular Junctions (NMJs)

Immunochemistry and NMJ analysis were performed following a modified protocol described in detail previously (Cobb, M. S., et al., 2013; Ling, K. K., et al., 2012). Three animals from each treatment and control groups at age P12 were anaesthetized by anesthetic inhalant Isoflurane® USP, VetOne™ (1-chloro-2, 2,2-trifluoroethyl difluoromethyl ether; 50 mg/kg) followed by transcardiac perfusion with Phosphate Buffered Saline (PBS) solution (Dulbecco's, Gibco®, LifeTechnologies™ Carlsbad, Calif., USA), and fixed with 4% paraformaldehyde (Sigma-Aldrich, St. Louis, Mo., USA). Whole-mount preparations were done by dissecting and examining the longissimus capitis muscle. Tissues were stained using specific antibodies including anti-neurofilament (1:2000; Chemicon®, EMD Millipore, Billerica, Mass., USA) and anti-synaptophysin (1:200, LifeTechnologies™ Carlsbad, Calif., USA). Acetylcholine receptors (AChRs) were labeled with Alexa Fluor 594-conjugated α-bungarotoxin (LifeTechnologies™ Carlsbad, Calif., USA). Muscle preparations were viewed using a laser scanning confocal microscope (40× objective; 0.8NA; Zeiss LSM Model 510 META, Carl Zeiss, Jena, Germany, EU). From the confocal microscopy, Z-series stack images of immunostained whole-mount muscles were obtained at sequential focal planes 1 μm apart and merged using microscope integrated software and despeckled by ImageJ software, Fiji (Schindelin, J., et al., 2012).

RT-PCR Assays

Total RNA was isolated from brain tissues harvested on P7 and homogenized using TRIzol reagent (LifeTechnologies™ Carlsbad, Calif., USA). Two micrograms of total RNA was used to generate first-strand cDNA by using 100 ng of random primers, 2 microliters dNTP (10 mM) Mix; 4 microliters of 5× first-strand buffer, 1.0 microliter DTT (0.1 M) and 1.0 microliter SuperScript™ III Reverse Transcriptase (200 U per microliter) (LifeTechnologies™ Carlsbad, Calif., USA) at 50° C./50 min followed by reaction inactivation at 70° C./15 min. Cycling conditions were as follows: an initial denaturation step (94° C./3 min), 30 cycles (94° C./30 sec; 60° C./0.5 min; 72° C./1 min), and a final extension step (72° C./10 min). Reaction products were resolved by electrophoresis through a 2.0% agarose gel (GeneMate, BioExpress, Kaysville, Utah, USA) and visualized by ethidium bromide staining on FOTODYNE™ Imaging Systems (Hartland, Wis., USA). For cDNA controls specific plasmids pCIExSkip and pCIFL were used (Lorson, C. L., et al., 1999).

Western Blots

For the SMNΔ7 mouse Western blots, indicated tissues were collected at selected time points (P7) and immediately frozen in liquid nitrogen. Tissue samples were placed at −80° C. until ready for analysis. Roughly 100 mg of tissue was homogenized in JLB buffer (50 mM Tris-HCl pH 7.5, 150 mM NaCl, 20 mM $NaH_2(PO_4)$, 25 mM NaF, 2 mM EDTA, 10% glycerol, 1% Triton X100, and protease inhibitors (Roche, Indianapolis, Ind., USA)). Equal amounts of protein were separated on 12% SDS-PAGE gels. SMN immunoblots were performed using a mouse SMN specific monoclonal antibody (BD Biosciences, San Jose, Calif., USA) diluted 1:300 in TBST (Tris-buffered Saline Tween20 (10 mM Tris-HCl, pH7.5, 150 mM NaCl, 0.2% Tween20)) in 1.5% dry milk. Then blots were visualized by chemiluminescence on a Fujifilm imager LAS-3000 (FujiFilm$^{USA}$, Hanover Park, Ill., USA) and the corresponding software. To verify equal loading the Westerns were then stripped using $H_2O_2$ for 30 minutes at room temperature and re-probed with anti-β-actin rabbit and anti-rabbit HRP secondary antibody (Jackson ImmunoResearch Laboratories, Inc. West Grove, Pa., USA). Western blots were performed in quadruplicate or more and representative blots are shown.

Results

Figure 13:
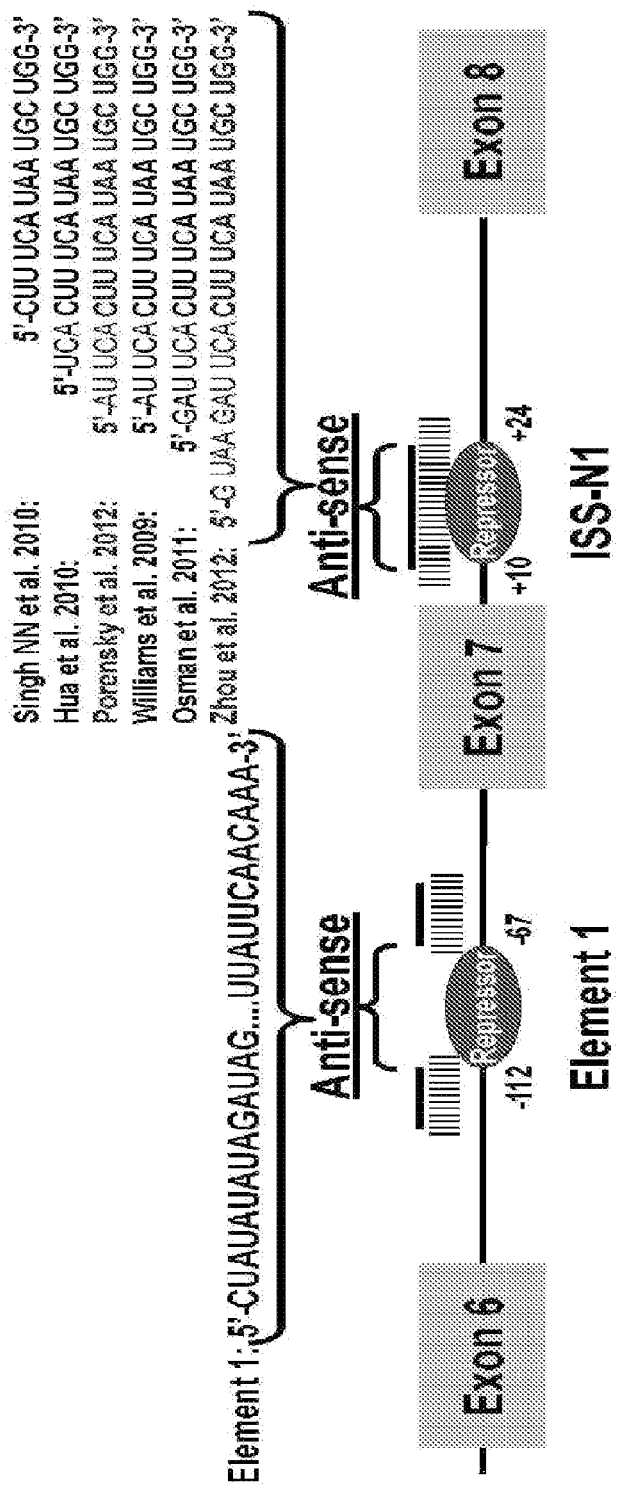
FIG. 13 illustrates targeting of the intronic repressor Element 1 with antisense oligonucleotides versus previously published ASO sequences targeting the intronic silencer ISS-N1. 5'-CUAUAUAUAGAUAG (SEQ ID NO: 25), UUAUUCAACAAA-3' (SEQ ID NO: 26), Singh N N et al. 2010 (SEQ ID NO: 27), Hua et al. 2010 (SEQ ID NO: 28), Porensky et al. 2012 (SEQ ID NO: 29), Williams et al. 2009 (SEQ ID NO: 30), Osman et al. 2011 (SEQ ID NO: 31), Zhou et al. 2012 (SEQ ID NO: 32).

FIG. 13 illustrates targeting of the intronic repressor Element 1 with morpholino modified ASOs. FIG. 13 is a schematic representation of specific morpholino-modified ASO targeting the intronic repressor Element 1 ($E1^{MO}$-ASO). A specific design of an $E1^{MO}$-ASO is illustrated with the antisense domains consisting of two non-sequential target antisense sequences targeting the intronic Element 1 repressor. In addition, several previously published ASO sequences with different modified chemistries and targeting the intronic silencer ISS-N1 are also shown.

Figure 14:
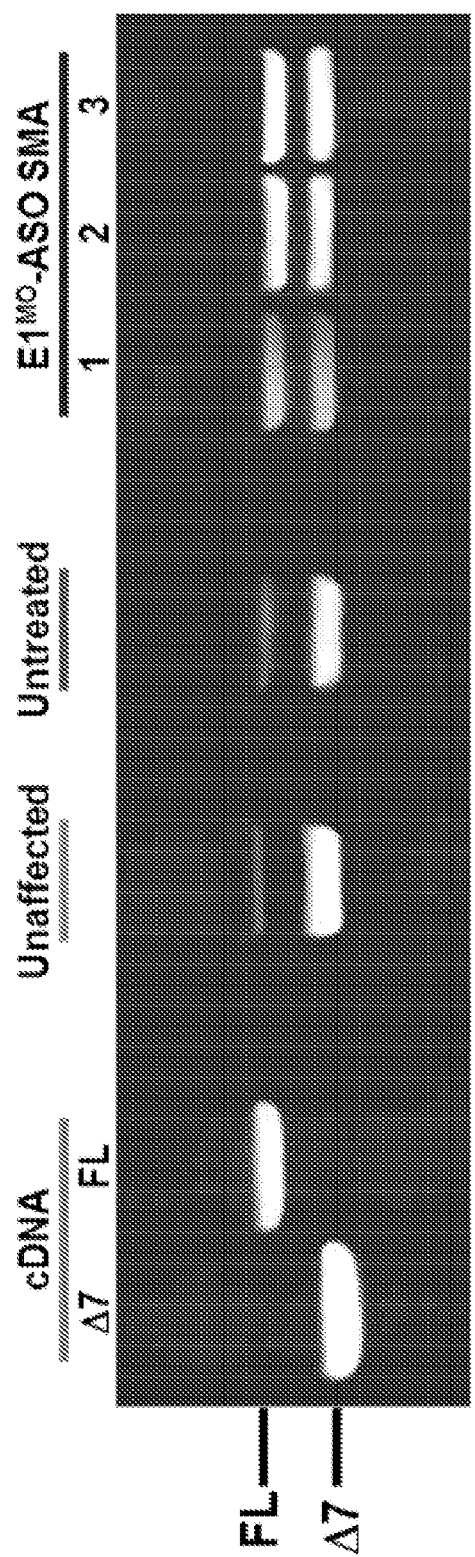
FIG. 14 shows an increase in full-length SMN transcript after $E1^{MO}$-ASO treatment in Example 3.

FIG. 14 shows an increase in full-length SMN transcript after $E1^{MO}$-ASO treatment. RT-PCR image showing full-length SMN in three individual animals. The plasmids pCIExSkip and pCIFL were used for cDNA controls.

Figure 15:
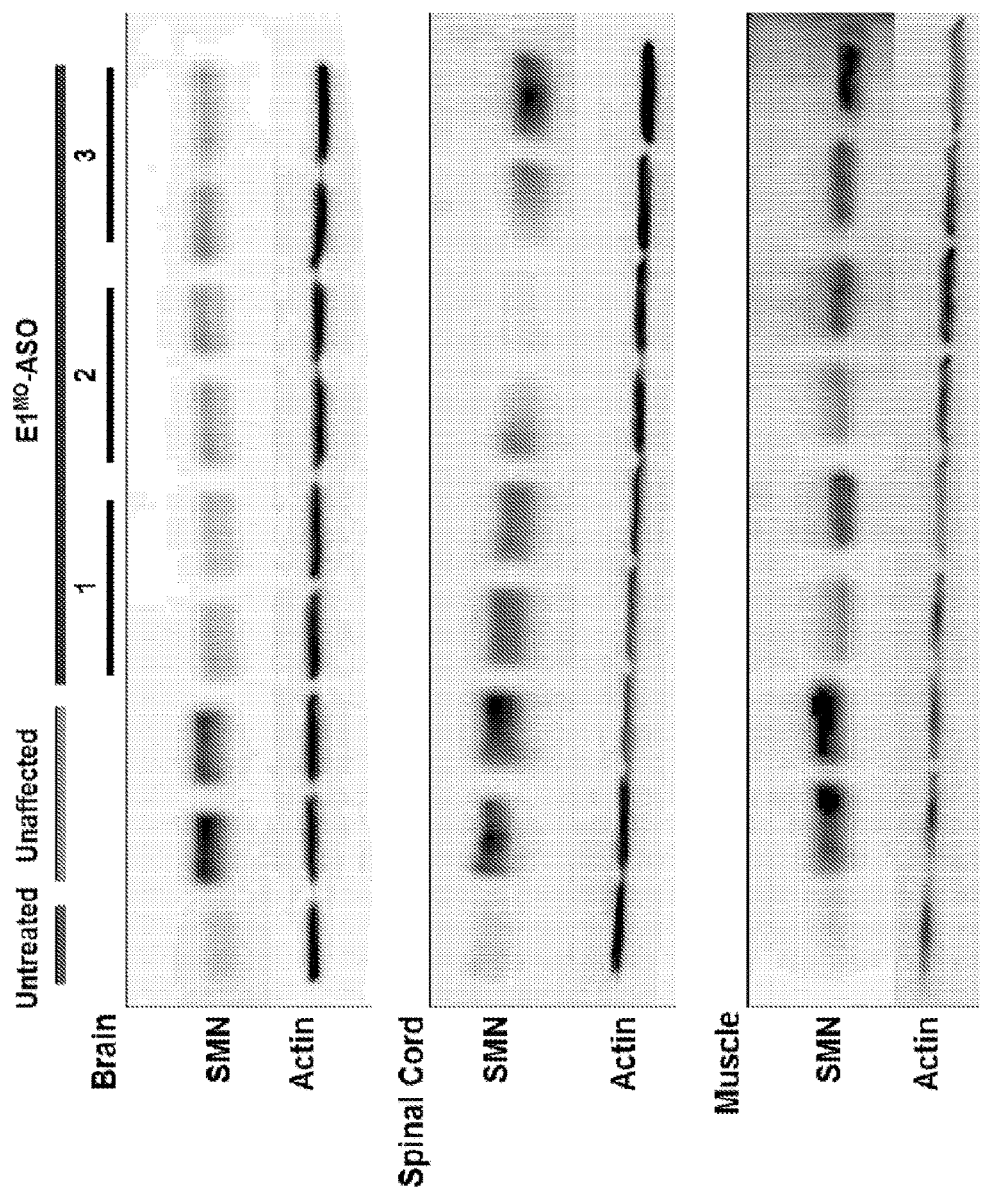
FIG. 15 shows that injection of morpholino based ASO targeting the Element1 repressor increased total SMN protein in the Δ7SMA mouse model in Example 3.

FIG. 15 shows that injection of morpholino based ASO targeting the Element1 repressor increased total SMN protein in the Δ7SMA mouse model. Single ICV injection of E1$^{MO}$-ASO increase SMN protein levels. Western blots (n=5) for each treatment group were performed on brain, spinal cord and muscle tissues at P7.

Figure 16A:
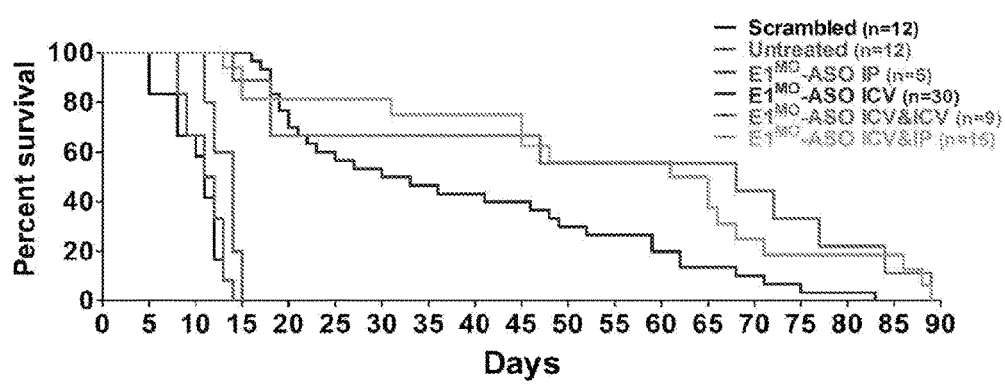
FIG. 16a shows that severe SMNΔ7 SMA mice showed significant improvement in survival and longevity after injections with $E1^{MO}$-ASO oligos in Example 3.
Figure 16B:
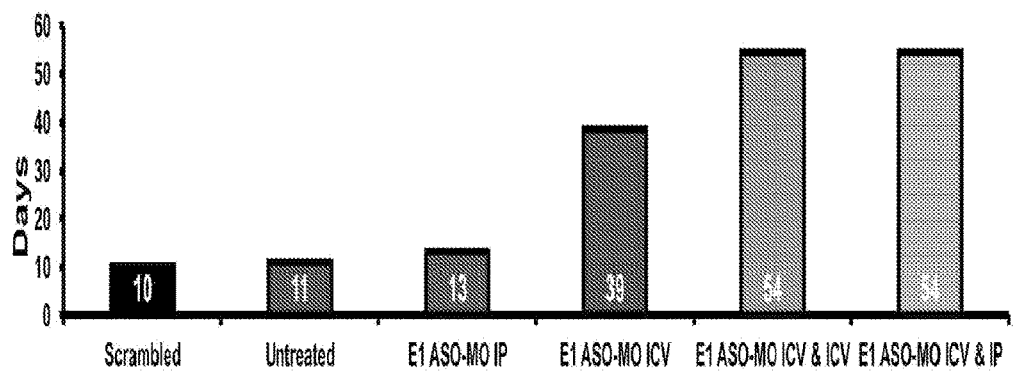
FIG. 16b shows survival curves demonstrating a significant increase in life expectancy for $E1^{MO}$-ASO ICV, ICV&ICV and ICV&IP injected animals in Example 3.

FIG. 16a shows that severe SMNΔ7 SMA mice showed significant improvement in survival and longevity after injections with E1$^{MO}$-ASO oligos. Kaplan-Meier survival curves were constructed from the various treatment groups and the routes of delivery as indicated. Log-rank (Mantel-Cox) statistics were applied for comparisons between groups where p<0.0001 for all treatment groups compared to untreated animals, with the exception of E1$^{MO}$-ASO IP injected animals when compared to the untreated controls (p=0.0526). FIG. 16b shows survival curves demonstrating a significant increase in life expectancy for E1$^{MO}$-ASO ICV, ICV&ICV and ICV&IP injected animals with increases in median survival to 39, 54 and 54 days respectively. Some tail necrosis was displayed by the ICV injected SMA animals around day 40-45 (not shown).

Figure 17:
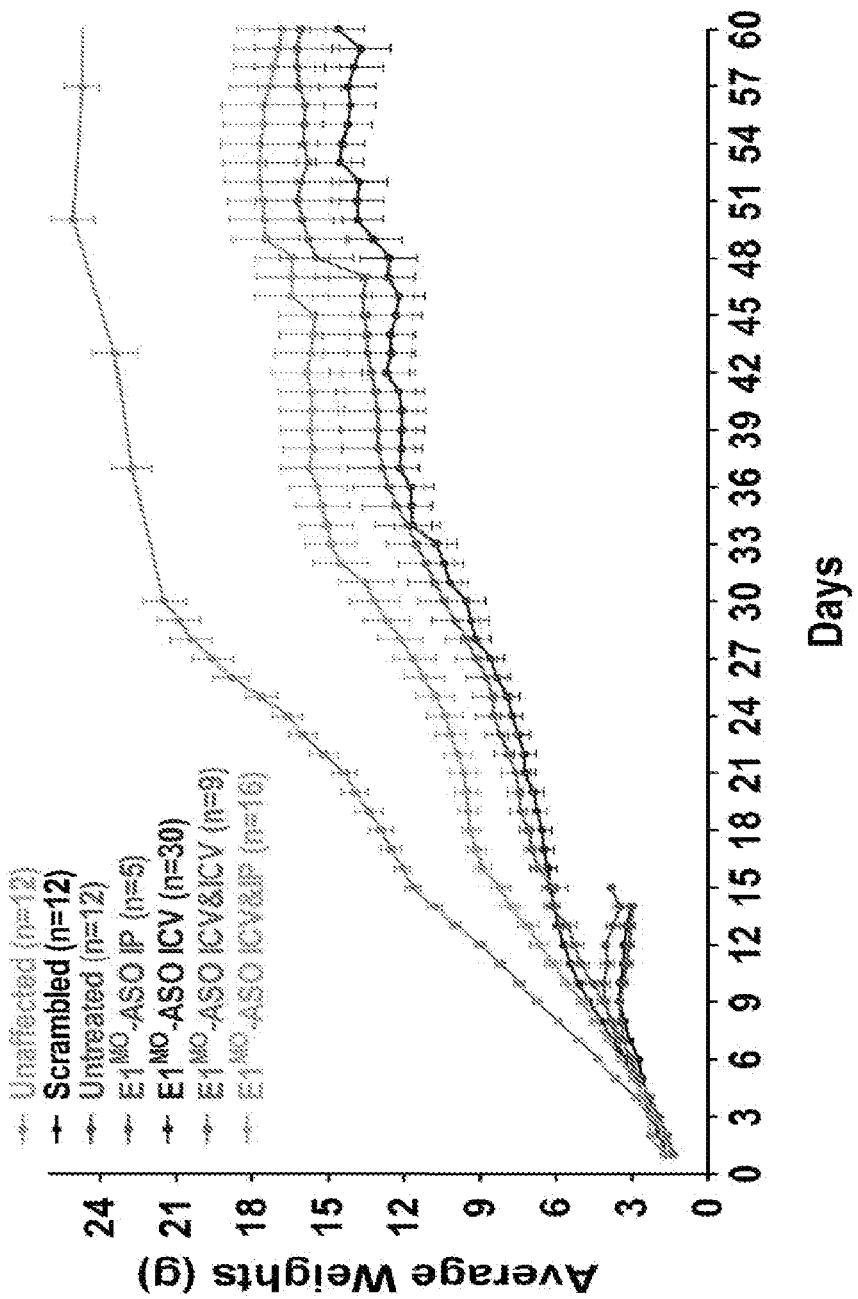
FIG. 17 shows that $E1^{MO}$-ASO treatment results in a significant weight gain in Example 3.

FIG. 17 shows that E1$^{MO}$-ASO treatment results in a significant weight gain. Referring to FIG. 17, starting at P7, E1$^{MO}$-ASO injected animals were heavier than untreated, scrambled and IP only injected SMA controls. Total body weight was measured daily for all animal groups post injection.

Figures 18A, 18B:
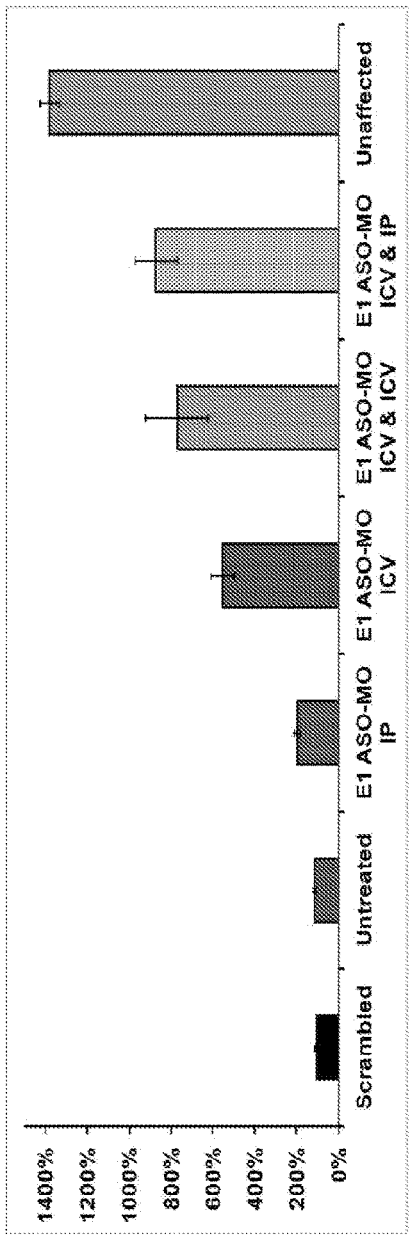

FIG. 18a shows the percent weight gained from birth to peak was also compared between groups treated. FIG. 18b shows statistical significance between each treatment group. Statistical significance in percent weight gain from birth to peak after E1$^{MO}$-ASO treatment. P-values are shown for each treatment group. Student's t-Test was used to compare each group against all treatment and control animals. P values were rounded to the sixth decimal point.

Figure 19:
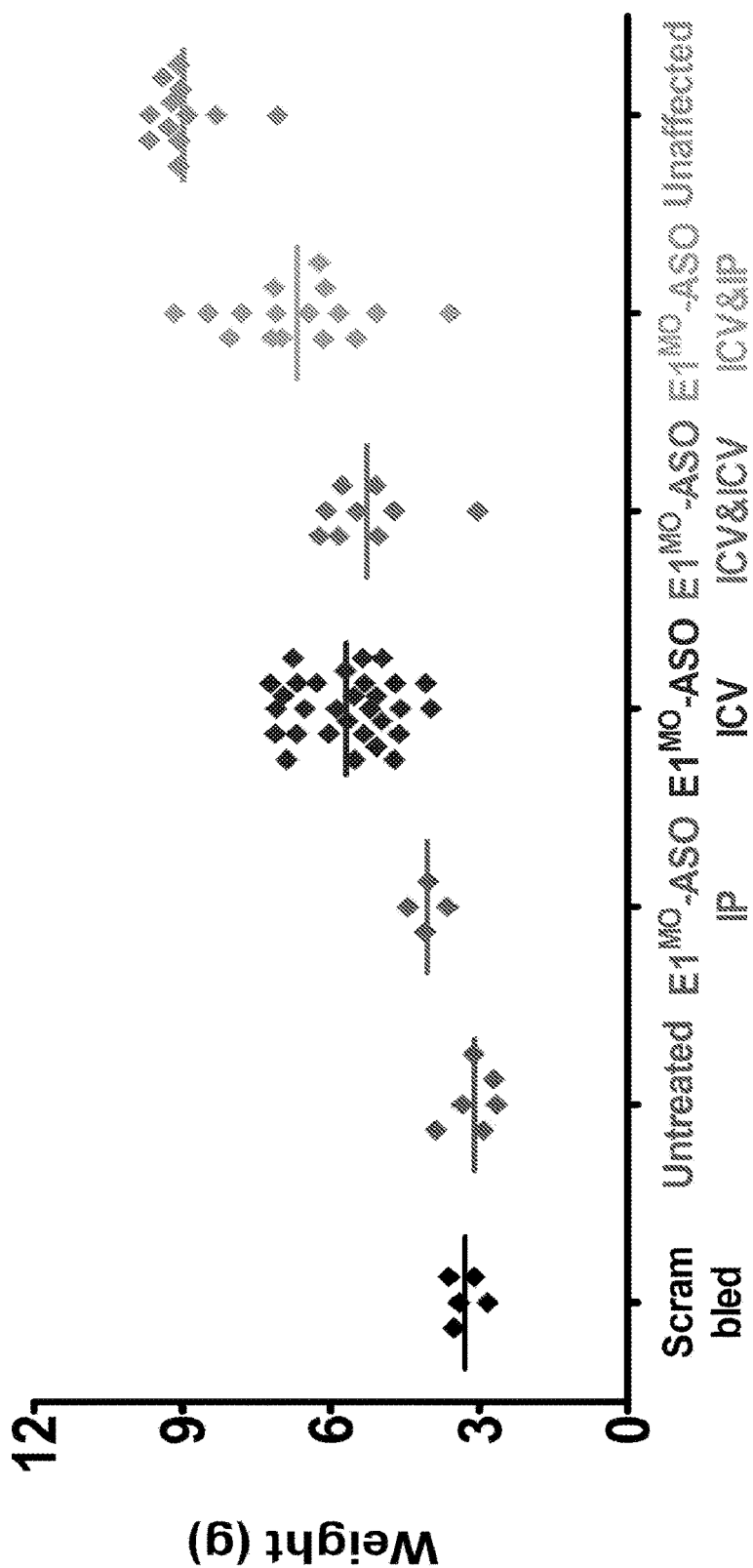
FIG. 19 shows individual weights on P12 for all controls and animals treated with E1$^{MO}$-ASO in Example 3.

FIG. 19 shows individual weights on P12 for all controls and animals treated with E1$^{MO}$-ASO.

Figure 20:
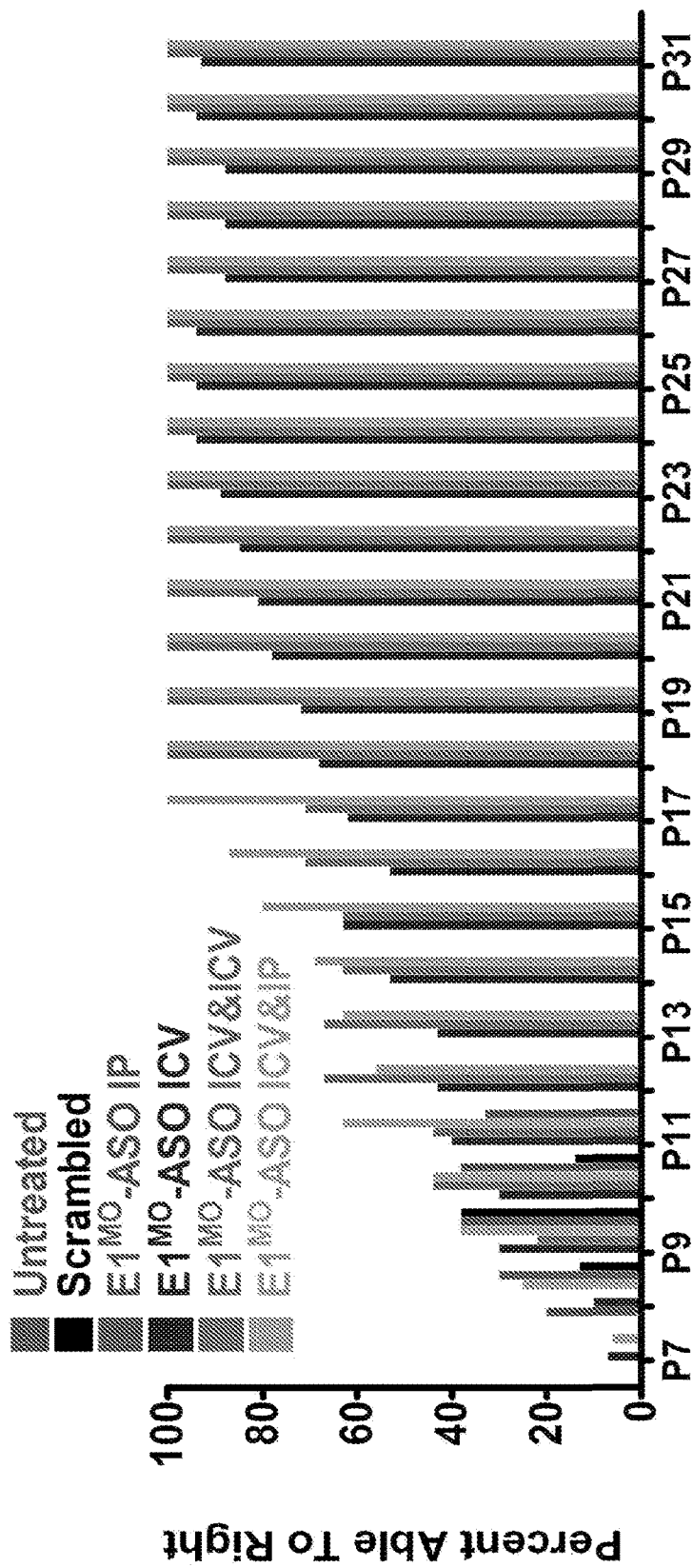
FIG. 20 is a bar graph showing the percent of all tested animal groups able to right themselves from a prone position in Example 3.

FIG. 20 is a bar graph showing the percent of all tested animal groups able to right themselves from a prone position. By P14, more than fifty percent of all ICV, ICV&ICV, and ICV&IP injected were able to right themselves.

Figure 21A:
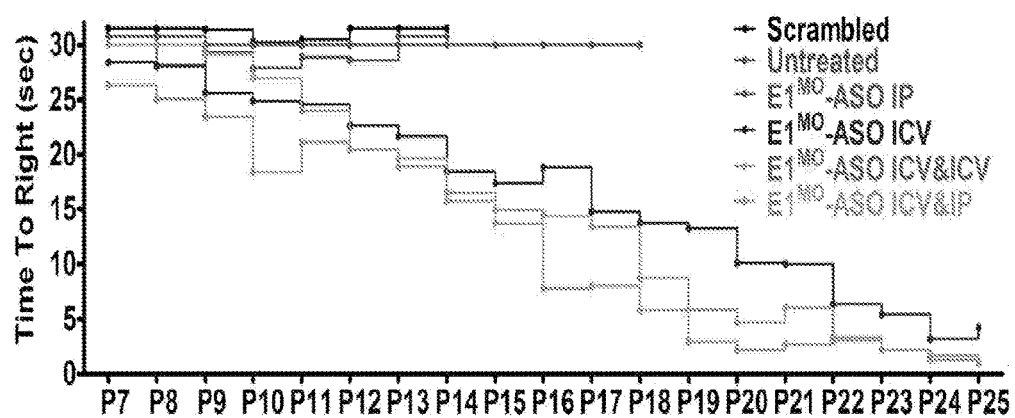
FIG. 21a is a graph representing raw data of the average time to right from P7 to P25 in Example 3.
Figure 21B:
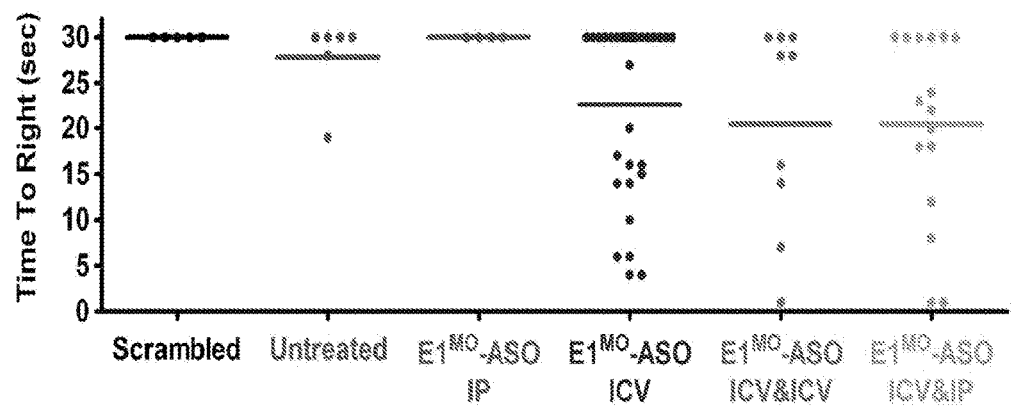
FIG. 21b is a scatter plot of TTR performance of mice injected with E1$^{MO}$-ASO in Example 3.

FIG. 21a is a graph representing raw data of the average time to right from P7 to P25. Animals injected with E1$^{MO}$-ASO ICV, E1$^{MO}$-ASO ICV&ICV and E1$^{MO}$-ASO ICV&IP were able to right themselves within 20 seconds after 2 weeks. FIG. 21b is a scatter plot of TTR performance of mice injected with E1$^{MO}$-ASO. To highlight the performance of individual mice, TTR values are shown for P12.

Figure 22:
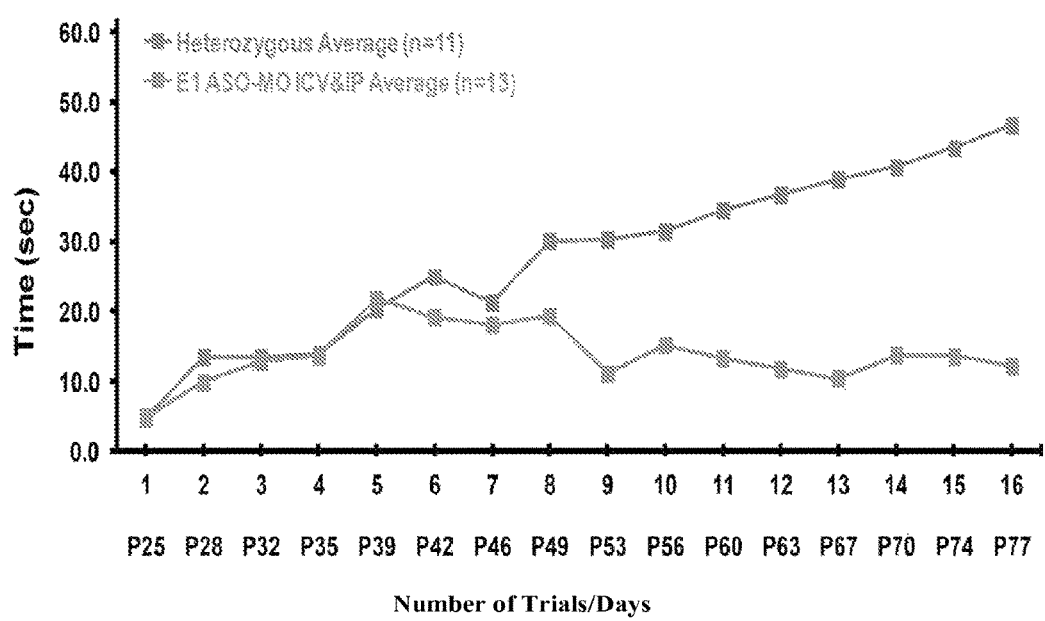
FIG. 22 shows grip strength measurements in grams in Example 3.

FIG. 22 shows grip strength measurements in grams. Treated animals were compared to their unaffected littermates. Measurements were taken from P25 through P77.

Figure 23:
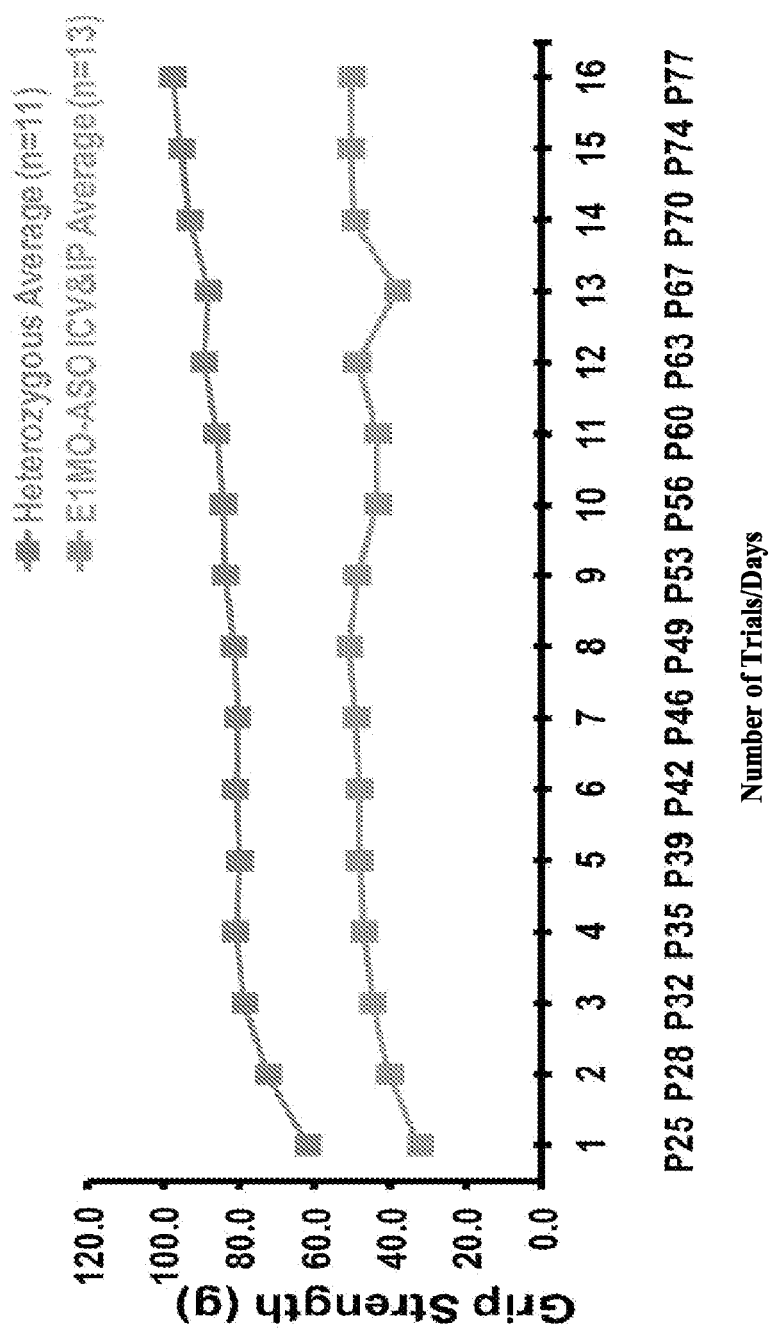
FIG. 23 shows results of the rotarod performance test in Example 3.

FIG. 23 shows results of the rotarod performance test. The test was used to measure riding time parameter (in seconds) of the E1$^{MO}$-ASO treated animals and compared with the times of their age-matched unaffected controls. Measurements were taken from P25 through P77.

Improvement in neuromuscular junctions (NMJs) pathology. The longissimus capitis (LC) muscles from ICV injected and control animals at P12 were immunostained for nerve terminals with anti-neurofilament/anti-synaptophysin [Nerve/Syn] and motor endplates with α-bungarotoxin. While the untreated SMNΔ7 mice displayed typical severe denervation, E1$^{MO}$-ASO treatment substantially restored NMJ's pretzel-like structures (not shown).

Figure 24A:
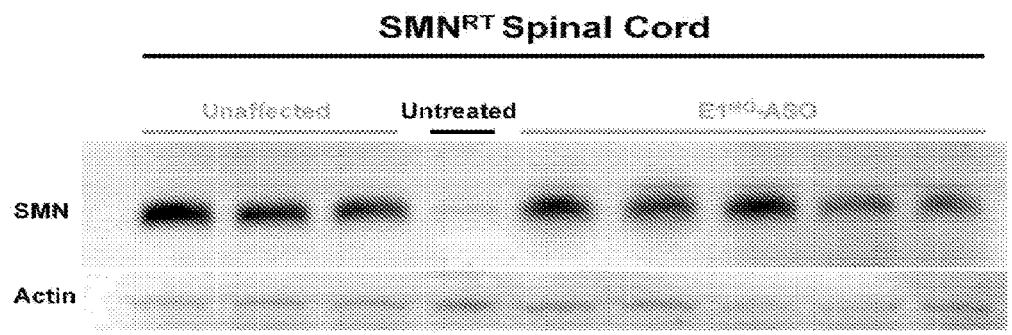
FIG. 24a is a Western blot (n=3) showing increased SMN in spinal cord tissue of five (5) ICV injected animals with E1$^{MO}$-ASO in Example 3.
Figure 24B:
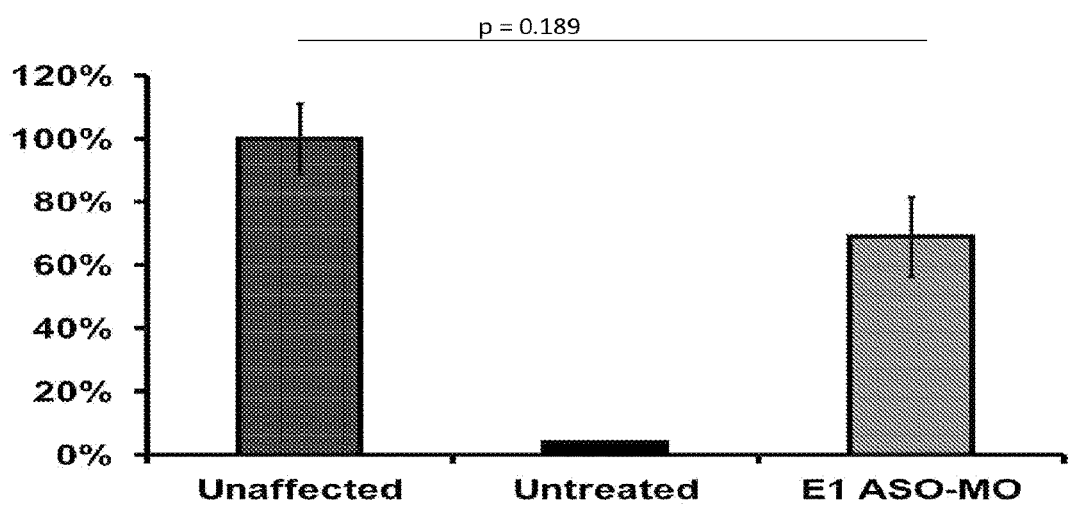

SMN protein induction in the milder mouse model of SMA (SMN$^{RT}$). FIG. 24a is a Western blot (n=3) showing increased SMN in spinal cord tissue of five (5) ICV injected animals with E1$^{MO}$-ASO. FIG. 24b shows Western blot quantification. Bar graph showing no significant difference in protein induction between unaffected and treated milder type SMA$^{RT}$ mice.

Figure 25:
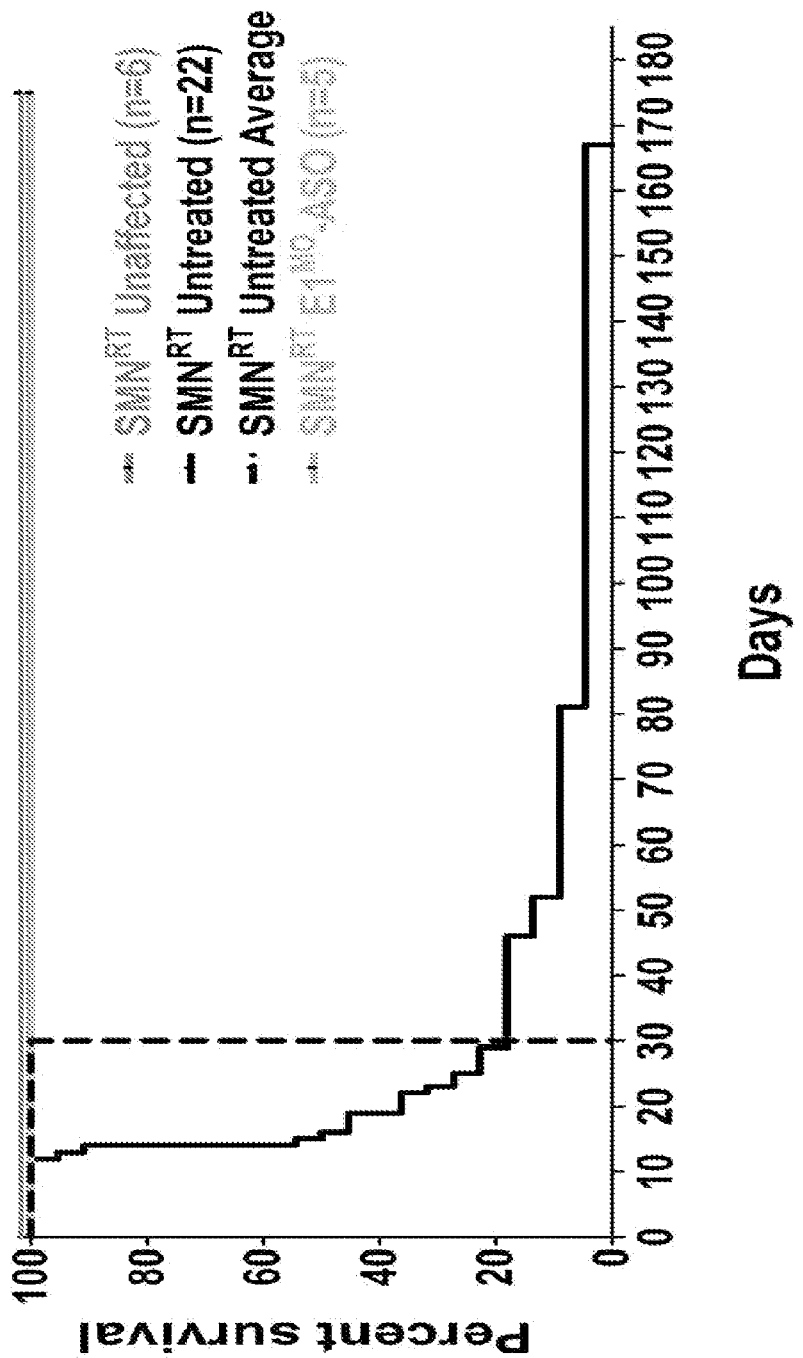
FIG. 25 shows that the treated SMN$^{RT}$ animals (labeled "SMN$^{RT}$ E1$^{MO}$-ASO") and the unaffected littermates (labeled "SMN$^{RT}$ Unaffected") were substantially more vigorous and lived more than 180 days compared to the untreated mice (labeled "SMA$^{RT}$ Untreated") in Example 3.

SMN$^{RT}$ mice injected with E1$^{MO}$-ASO, showed significant improvement in survival and weight gain. FIG. 25 shows that the treated SMN$^{RT}$ animals (labeled "SMN$^{RT}$E1$^{MO}$-ASO") and the unaffected littermates (labeled "SMN$^{RT}$ Unaffected") were substantially more vigorous and lived more than 180 days compared to the untreated mice (labeled "SMA$^{RT}$ Untreated"). The Kaplan-Meier survival curve depicts an identical in life expectancy for unaffected and treated SMN$^{RT}$ mice. Animals were culled after 180 days.

Figure 26:
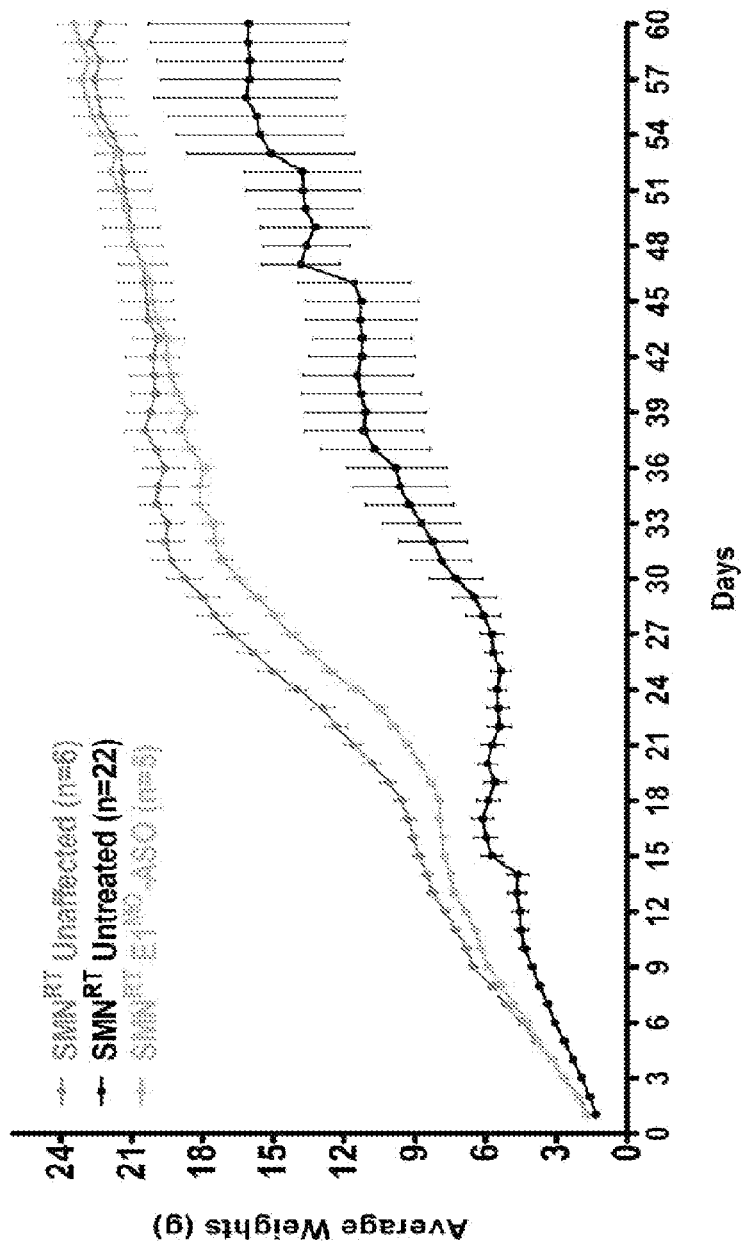
FIG. 26 shows a significant increase in the average weight of SMN$^{RT}$ animal model after treatment with E1$^{MO}$-ASO in Example 3.

FIG. 26 shows a significant increase in the average weight of SMN$^{RT}$ animal model after treatment with E1$^{MO}$-ASO.

Figure 27:
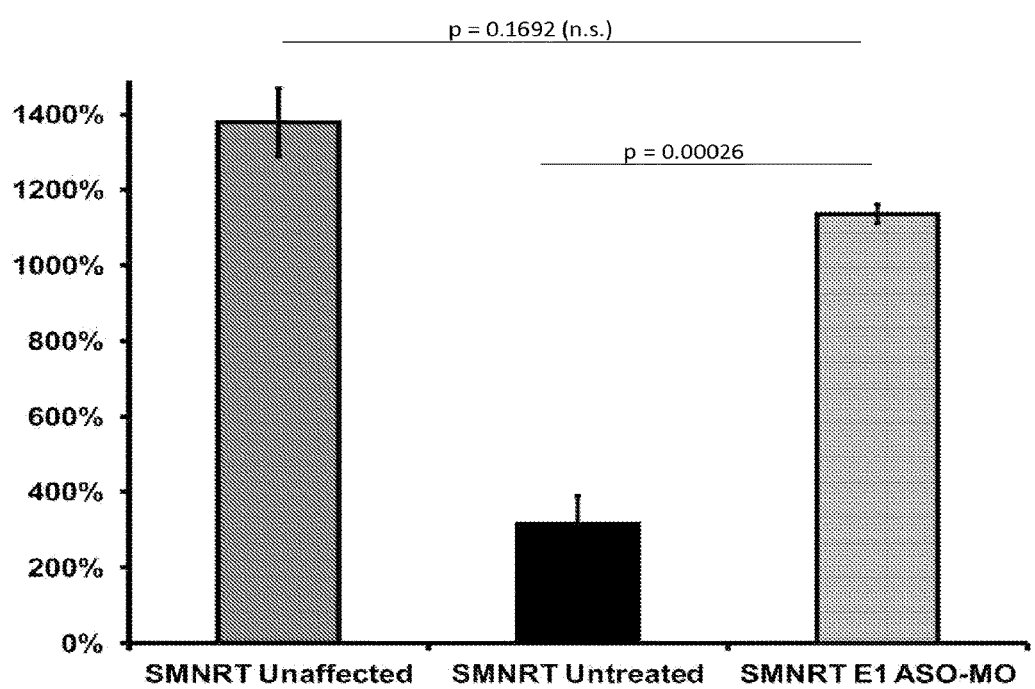
FIG. 27 show a comparison of the percent weight gained from birth to peak between animal groups in Example 3.

FIG. 27 show a comparison of the percent weight gained from birth to peak between animal groups. For statistical significance between each treatment group, Student's T-Test was used and p-values are shown for E1$^{MO}$-ASO SMN$^{RT}$ animals.

Figure 28:
FIG. 28 shows individual weights on P12 in Example 3.

FIG. 28 shows individual weights on P12. Weights of treated mice are comparable to the weights of unaffected age-matched littermates.

Figure 29:
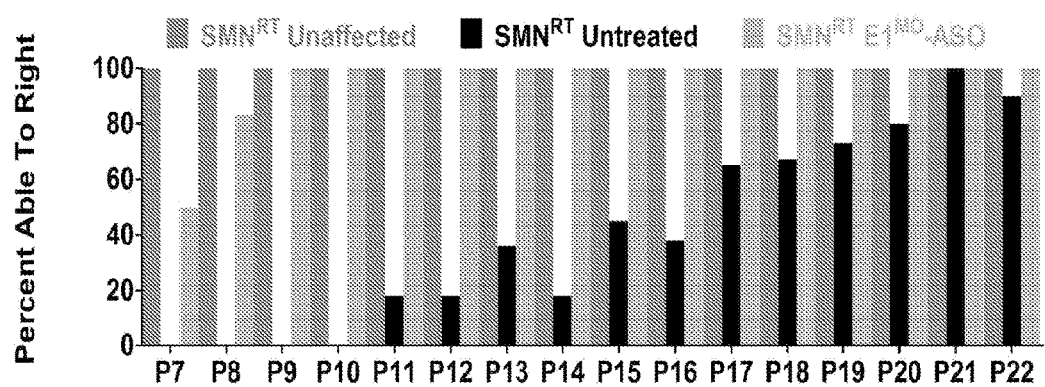
FIG. 29 shows the percent of the tested animals able to right themselves compared to untreated mice where the TTR reflex is delayed in Example 3.

TTR, muscle strength, balance, and motor-planning measurements show significant improvement in E1$^{MO}$-ASO treated SMN$^{RT}$ mice. FIG. 29 shows the percent of the tested animals able to right themselves compared to untreated mice where the TTR reflex is delayed. By P9, all treated and unaffected animals were able to right themselves.

Figure 30:
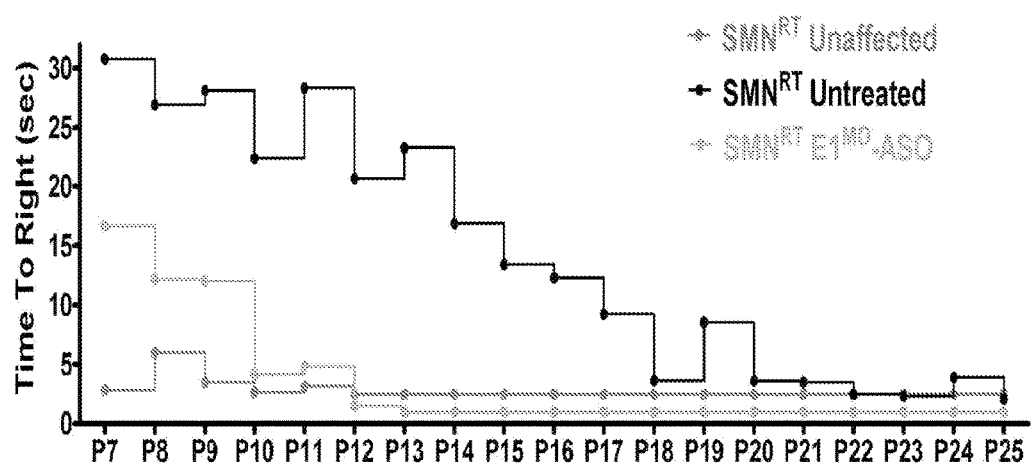
FIG. 30 shows the average time to right from P7 to P25 for all experimental groups in Example 3.

FIG. 30 shows the average time to right from P7 to P25 for all experimental groups. SMN$^{RT}$ mice injected with E1$^{MO}$-ASO were able to right themselves within 10 seconds after 10 days.

Figure 31:
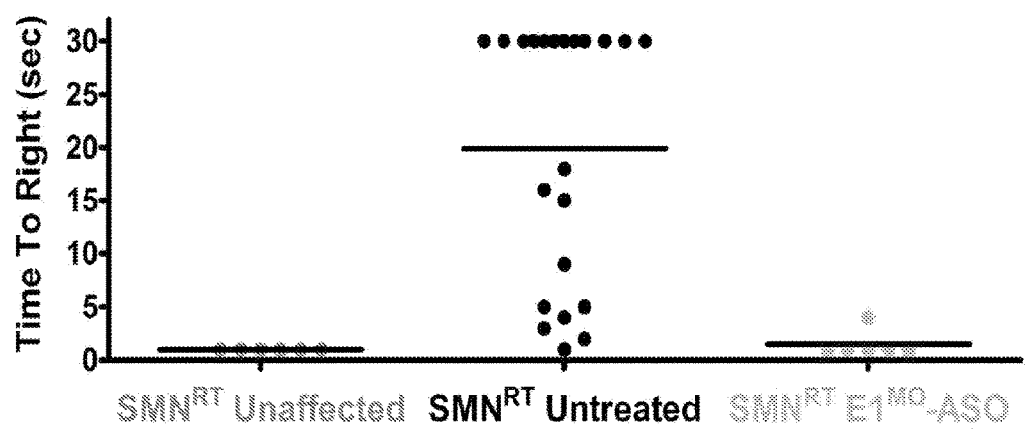
FIG. 31 is a scatter plot of TTR performance of SMN$^{RT}$ mice injected with E1$^{MO}$-ASO in Example 3.

FIG. 31 is a scatter plot of TTR performance of SMN$^{RT}$ mice injected with E1$^{MO}$-ASO. Time-to-right performance of individual mice at age P12 shows that treated animals can successfully turn themselves within 5 seconds.

Figure 32:
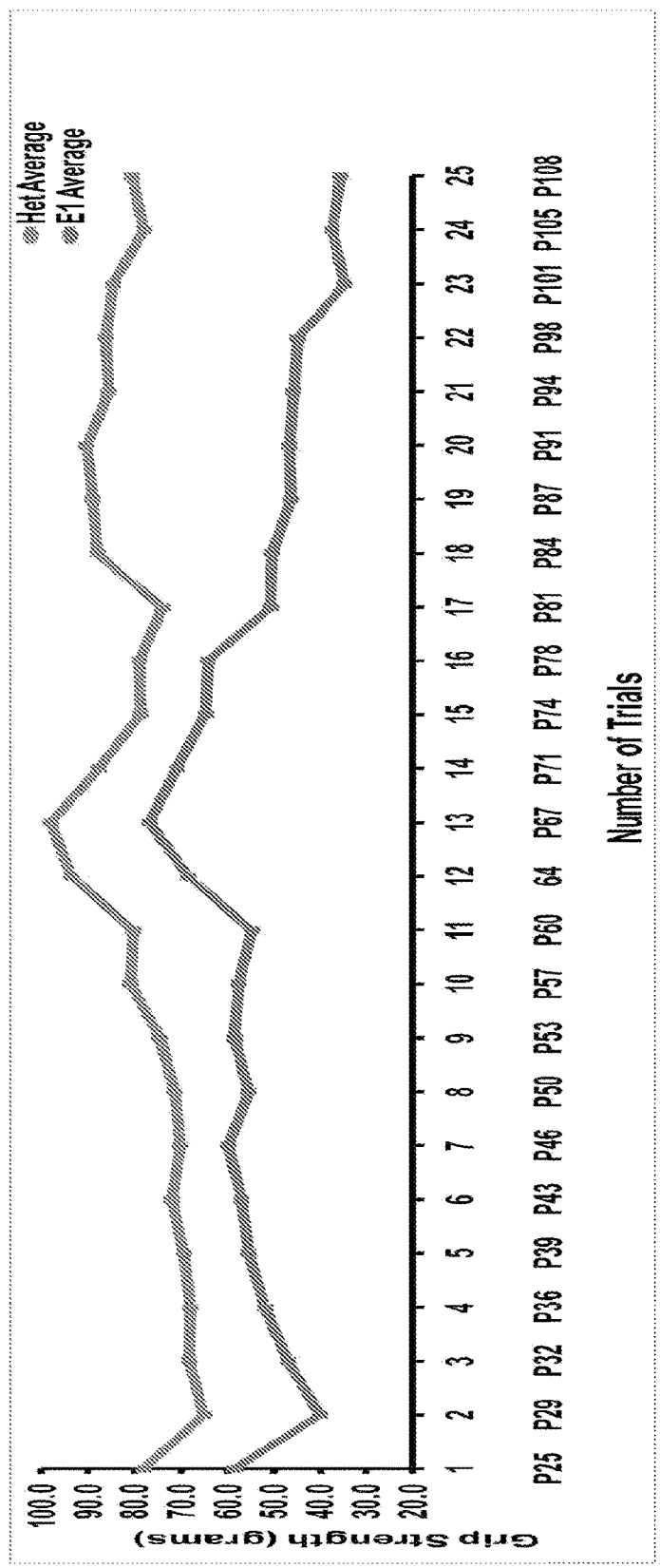
FIG. 32 shows grip strength measurements in grams in Example 3.

FIG. 32 shows grip strength measurements in grams. Treated animals were compared to their unaffected littermates. Measurements were taken from P25 through P108.

Figure 33:
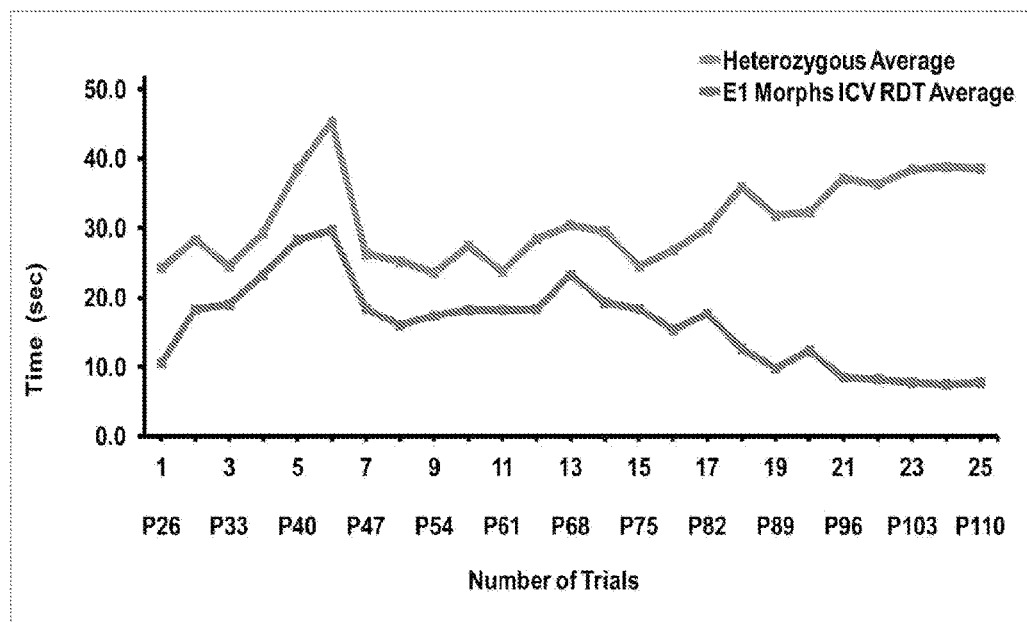
FIG. 33 shows results of the rotarod performance test in Example 3.

FIG. 33 shows results of the rotarod performance test. The test was used to measure riding time parameter (in seconds) of the E1$^{MO}$-ASO treated animals and compared with the times of their age-matched unaffected controls. Measurements were taken from P26 through P110.

Figure 34:
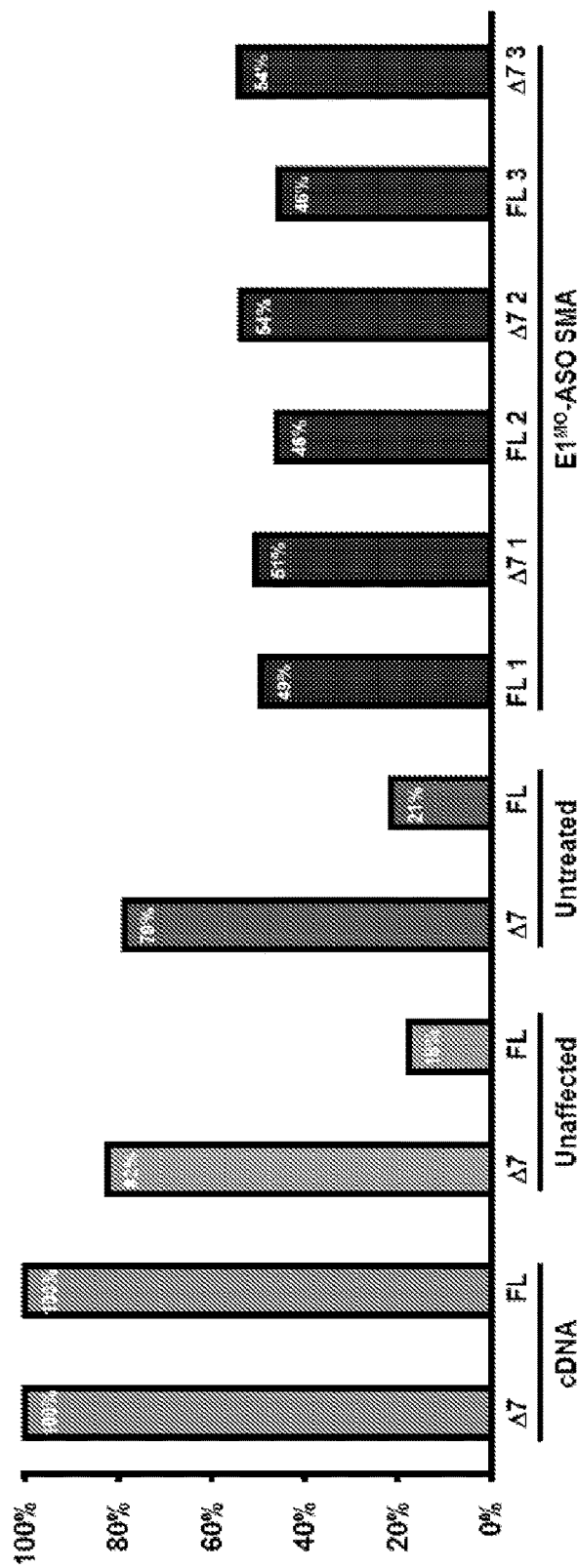
FIG. 34 is RT-PCR quantification showing the percent increase in full length SMN transcript in three SMA animals after treatment with E1$^{MO}$-ASO in Example 3.

FIG. 34 is RT-PCR quantification showing the percent increase in full length SMN transcript in three SMA animals after treatment with E1$^{MO}$-ASO.

Figure 35:
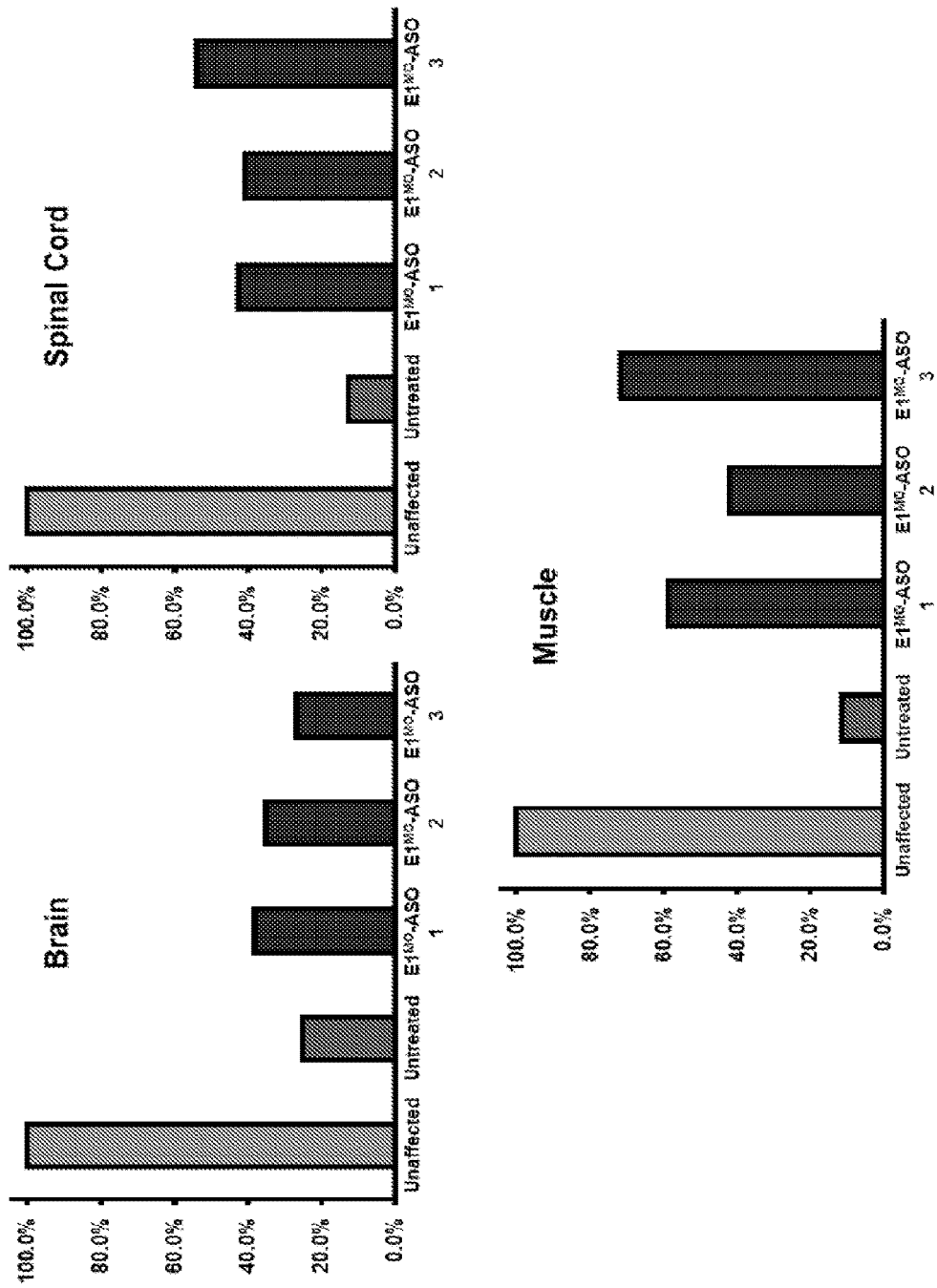
FIG. 35 is Western blot quantification showing the percent increase in SMN protein induction was compared to the unaffected and untreated control group and plotted in a bar graph (n=5) in Example 3.

FIG. 35 is Western blot quantification showing the percent increase in SMN protein induction was compared to the unaffected and untreated control group and plotted in a bar graph. (n=5).

Delayed tail necrosis in E1$^{MO}$-ASO ICV/IP injected animals. After delivery via the combinatorial routes of ICV and IP injections, the treated animals exhibited a delayed tail necrosis (day 60-65) (not shown). E1$^{MO}$-ASO ICV injected SMN$^{RT}$ animals were indistinguishable from their unaffected littermates in movement and behavior pattern. Necropsy of male SMN$^{RT}$ mouse treated with E1$^{MO}$-ASO at age 175 days showed significant internal organ abnormalities such as deformed heart, subcutaneous fluid retention, and smaller kidneys. Enlarged and swollen bladder were clearly evident (not shown).

Element 1 as an ASO Target

To expand the repertoire of potential targets for SMA therapeutics, Morpholino-modified ASOs (E1$^{MO}$-ASOs) were developed that target the E1 repressor, a region distinct from the ISS-N1 repressor which has been the focus of the overwhelming majority of ASO strategies (FIG. 13).

Following a single injection into the central nervous system via intracerebroventricular (ICV) delivery of the E1$^{MO}$-ASO, pre-mRNA exon-skipping from the SMN2 transgene was significantly reduced in total RNA isolated from brain tissue, resulting in a nearly 3-4 fold increase in full-length SMN transcript in each of three animals examined.

FIG. 14 shows the increase in full-length SMN transcript after E1$^{MO}$-ASO treatment. RT-PCR image showing full-length SMN in three individual animals. The plasmids, pCIExSkip and pCIFL, were used for cDNA controls.

The mice used in this experiment were phenotypically wild type (unaffected), but carried the human genomic SMN2 gene. To determine if SMN levels increased similarly, a single ICV injection was delivered to SMNΔ7 (SMNΔ7$^{+/+}$; SMN2$^{+/+}$; Smn$^{-/-}$) pups on P2 and protein extracts were collected from brain, spinal cord, and skeletal muscle (*Musculus gastrocnemius*). The SMNΔ7 model, which has an average life span of 12-14 days, has been extensively characterized and utilized for a number of translational studies (Le, T. T., et al., 2005; Osborne, M. and Lutz, C., 2013; Lorson, M. A. and Lorson, C. L., 2012). In each treated animal examined, SMN protein levels were elevated several fold compared to untreated SMA animals, although wildtype tissue still contained slightly higher levels of SMN.

Phenotypic Correction in Severe SMA Mice

To determine whether delivery of the E1$^{MO}$-ASO to SMA mice on P2 improved the phenotype; survival, weight gain, righting reflexes and strength measurements were collected. A relatively low dose (2 mM) of ASO was selected, comparable to the "low" dose from a previously published report examining ISS-N1 ASOs (Porensky, P. N., et al., 2012). Untreated SMA mice lived less than 2 weeks, similar to a cohort treated with a control ASO consisting of the scrambled sequence. Similarly, delivery of the E1$^{MO}$-ASO via a single intraperitoneal (IP) injection failed to extend survival beyond 1-2 days. However, a single ICV injection of E1$^{MO}$-ASO led to nearly a 400% improvement in life span, with more than one third of the treated animals living beyond 50 days. When we looked at the life span of the negative control group animals, we observed no difference between our untreated and the scrambled Morpholino injected animals. SMA animal models exhibit extensive peripheral defects, particularly in severe models. To determine whether E1$^{MO}$-ASO treatment would rescue peripheral defects, a combinatorial treatment of ICV and IP injections was performed: two injections of the 2 mM ASO were delivered via ICV and an IP injection. In a separate cohort, two ICV injections were administered separated by 12 hours. The double-dosing resulted in a similar extension in survival, out to an average of 54 days, with more than one quarter of the animals living beyond 70 days. While the treated mice were highly ambulatory, distal necrosis, particularly of the tail, was observed in nearly all of the longer lived animals. In the ICV treated cohort, necrosis initiated at approximately P40-45, while ICV/IP treatment delayed necrosis onset to approximately P60. Collectively, these results demonstrate that the E1$^{MO}$-ASO can significantly extend survival in a severe mouse model of SMA.

E1$^{MO}$-ASO treatment resulted in significant weight gain compared to either untreated, scramble or IP-only ASO treated cohorts. The ICV/IP treated animals gained the most weight compared to the ICV or ICV/ICV groups, resulting in animals that achieved 15-18 grams. This was in stark contrast to the untreated, scramble or IP-only ASO treated cohorts that failed to thrive and were unable to achieve 5 grams. An additional measure of phenotypic correction used in the SMA field is the timed-righting response. Animals are placed on their backs and the time it takes to stand on four legs is recorded, as well as failed attempts. In the ICV, ICV/ICV, and ICV/IP cohorts, SMA treated animals improved significantly based upon the percentage of animals that could successfully turn over as well as the speed at which the animals successfully righted themselves.

Typically, SMA animals do not live long enough to perform gross motor function tests such as rotarod and grip strength; however, E1$^{MO}$-ASO treated mice lived long enough and were healthy enough to perform these assays. Following a one week period to acclimate to the equipment, grip strength and rotarod performance was collected for 16 consecutive days. Grip strength analysis revealed that the SMA E1$^{MO}$-ASO treated animals performed consistently, albeit with less force, compared to wild type animals. Rotarod performance also demonstrated that the ASO-rescued animals were not fully corrected compared to wild type animals especially at later time points. While the treated animals were never fully corrected compared to wild type animals, it is important to stress that their untreated (or scramble-treated cohorts) were dead weeks prior to these studies. This increasing discrepancy could in part be due to the development of tail necrosis as flexibility and/or loss of the tail would impact balance and rotarod performance.

An important hallmark of the SMA phenotype that directly relates to disease pathogenesis is the integrity of the neuromuscular junctions (NMJs). As expected, NMJs from untreated SMA mice appear immature, poorly developed and there was little overlap between the pre- and post-synaptic endplate. In contrast, the wild type and E1$^{MO}$-ASO-treated tissues exhibit well developed NMJs with a high degree of connectivity between the axons and the post-synaptic endplate. These results are consistent with the significant correction of the SMA phenotype at the organismal level and provide evidence that a molecular correction of SMN2 splicing using an E1$^{MO}$-ASO can profoundly reverse the severe SMA phenotype observed in SMNΔ7 mice.

Phenotypic Correction in Intermediate SMA Mice

Testing therapeutics in more than one model of disease validates the molecular engagement of a specific target, demonstrates applicability to a broader range of the patient population, and sheds light upon the biology of the disease. To address these important parameters, a newly developed intermediate model of disease was examined. This model, SMN$^{RT}$, expresses low levels of SMN, lives approximately 32 days, and exhibits an intermediate phenotype in most cellular and organismal parameters of disease (Cobb, M. S., et al., 2013). Following a single ICV injection of the E1$^{MO}$-ASO (2 mM), SMN protein was increased significantly, approximately 8-10 fold above untreated levels in spinal cord extracts. To verify whether ICV delivery of E1$^{MO}$-ASO also extended survival of the milder form SMA animals, lifespan for the treatment groups were analyzed by Kaplan-Meier survival curve and compared to the lifespan of the animals from the control groups. ICV injections of the E1$^{MO}$-ASO significantly increased the average lifespan of the SMN$^{RT}$ mice, compared to their aged-matched untreated control animals. In fact, all E1$^{MO}$-ASO treated animals were still alive at P175, at which point the experiment was stopped and animals were euthanized. The treated SMN$^{RT}$ mice were phenotypically indistinguishable from their unaffected age-matched littermates within the first two months of their life span. Consistent with an early and robust increase of SMN, treated SMN$^{RT}$ mice gained weight to near wild type levels during the first 4-5 weeks, and treated animals weighed as much as wild type animals beyond approximately 40 days. At nearly all time points, SMN$^{RT}$ treated mice were able to right themselves more rapidly than untreated mice and were as efficient as the wild type animals at time points beyond P10. Differences in grip strength and rotarod performance were detected over the trial period and as the animals aged, a greater disparity was observed between SMN$^{RT}$ treated mice and unaffected animals. Similar to the SMNΔ7 experiments, the initiation of tail necrosis later in life (at approximately P70-80 for the SMN$^{RT}$ mice) may have negatively impacted their ability to perform in these assays.

The dose that was initially administered was a 2 μM ICV injection. However, a doubling of this dose via two ICV injections or an ICV+IP dosing further enhanced survival. Interestingly, the ICV+IP dosing was the most efficacious presumably because the IP administration allowed for a greater distribution to peripheral tissues. It is also important to stress that the SMA mouse models do not necessarily reflect the frequency of peripheral complications in most SMA patients. Currently, all of the SMA models exhibit profound peripheral organ defects, while peripheral organ damage in SMA patients is largely restricted to very severe SMA cases.

While the invention has been described in connection with specific embodiments thereof, it will be understood that the inventive device is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth.

What claimed is:

1. A composition for blocking the repressive activity of the Element 1 of the SMN2 pre-mRNA, the composition comprising an antisense oligonucleotide that comprises the nucleic acid sequence SEQ ID NO: 17 (v1.11) or the nucleic acid sequence SEQ ID NO: 17 (v1.11) except for consisting of one nucleotide substitution.

2. The composition of claim 1 wherein the antisense oligonucleotide comprises the nucleic acid sequence SEQ ID NO: 17 (v1.11).

3. A method for blocking the repressive activity of the Element 1 of the SMN2 pre-mRNA, the method comprising the step of administrating to a subject the composition of claim 1.

4. The method of claim 3 wherein the composition is administered intracerebroventricularly, intraperitoneally, intravenously, or by a combinatorial administration thereof.

5. A method for treating Spinal Muscular Atrophy (SMA) in a human SMA patient, the method comprising the step of administrating to the patient an effective amount of a composition of claim 1.

6. The method of claim 5 wherein the composition is administered intracerebroventricularly, intraperitoneally, intravenously, or by a combinatorial administration thereof.

7. A method for blocking the repressive activity of the Element 1 of the SMN2 pre-mRNA, the method comprising the step of administrating to a subject the composition of claim 2.

8. The method of claim 7 wherein the composition is administered intracerebroventricularly, intraperitoneally, intravenously, or by a combinatorial administration thereof.

9. A method for treating Spinal Muscular Atrophy (SMA) in a human SMA patient, the method comprising the step of administrating to the patient an effective amount of a composition of claim 2.

10. The method of claim 9 wherein the composition is administered intracerebroventricularly, intraperitoneally, intravenously, or by a combinatorial administration thereof.

* * * * *